US012566947B2

(12) United States Patent
Isogawa et al.

(10) Patent No.: US 12,566,947 B2
(45) Date of Patent: Mar. 3, 2026

(54) IMAGE PROCESSING SYSTEM AND MEDICAL INFORMATION PROCESSING SYSTEM

(71) Applicants: KABUSHIKI KAISHA TOSHIBA, Tokyo (JP); CANON MEDICAL SYSTEMS CORPORATION, Otawara (JP)

(72) Inventors: Kenzo Isogawa, Yokohama (JP); Tomoyuki Takeguchi, Kawasaki (JP)

(73) Assignees: KABUSHIKI KAISHA TOSHIBA, Tokyo (JP); CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 18/392,105

(22) Filed: Dec. 21, 2023

(65) Prior Publication Data

US 2024/0127043 A1     Apr. 18, 2024

Related U.S. Application Data

(62) Division of application No. 18/084,863, filed on Dec. 20, 2022, now Pat. No. 11,886,978, which is a
(Continued)

(30) Foreign Application Priority Data

Jun. 1, 2017     (JP) ................................. 2017-108934

(51) Int. Cl.
G06N 3/048       (2023.01)
G06N 3/045       (2023.01)
(Continued)

(52) U.S. Cl.
CPC ............. *G06N 3/048* (2023.01); *G06N 3/045* (2023.01); *G06N 3/084* (2013.01); *G06N 3/09* (2023.01);
(Continued)

(58) Field of Classification Search
CPC ........ G06N 3/045; G06N 3/048; G06N 3/084; G06N 3/09; G06T 2207/20084;
(Continued)

(56) References Cited

U.S. PATENT DOCUMENTS

2016/0125572 A1*   5/2016   Yoo ........................... G06T 5/70
                                                          382/157
2016/0209995 A1*   7/2016   Jeon ........................ G16Z 99/00
(Continued)

FOREIGN PATENT DOCUMENTS

JP          3-167535 A        7/1991
JP          2006-140952 A     6/2006
JP          2016-168046 A     9/2016

OTHER PUBLICATIONS

Youssef et al. "Feature-Preserving Noise Removal," IEEE Transactions On Medical Imaging, vol. 34, No. 9, Sep. 2015 (Year: 2015).*
(Continued)

*Primary Examiner* — Kenny A Cese
(74) *Attorney, Agent, or Firm* — Oblon, McClelland, Maier & Neustadt, L.L.P.

(57) ABSTRACT

In one embodiment, an image processing system includes a memory and processing circuitry. The memory is configured to store a predetermined program. The processing circuitry is configured, by executing the predetermined program, to perform processing on an input image by exploiting a neural network having an input layer, an output layer, and an intermediate layer provided between the input layer and the
(Continued)

output layer, the input image being inputted to the input layer, and adjust an internal parameter based on data related to the input image, while performing the processing on the input image after training of the neural network, the internal parameter being at least one internal parameter of at least one node included in the intermediate layer, and the input parameter having been calculated by the training of the neural network.

10 Claims, 17 Drawing Sheets

Related U.S. Application Data division of application No. 15/994,161, filed on May 31, 2018, now Pat. No. 11,574,170.

(51) Int. Cl.
| | |
|---|---|
| *G06N 3/084* | (2023.01) |
| *G06N 3/09* | (2023.01) |
| *G06T 5/60* | (2024.01) |
| *G06T 5/70* | (2024.01) |
| *G16H 30/40* | (2018.01) |

(52) U.S. Cl.
CPC ................. *G06T 5/60* (2024.01); *G06T 5/70* (2024.01); *G16H 30/40* (2018.01); *G06T 2207/20084* (2013.01); *G06T 2207/30004* (2013.01)

(58) Field of Classification Search
CPC ... G06T 2207/30004; G06T 5/60; G06T 5/70; G16H 30/40
USPC ........................................................ 382/156
See application file for complete search history.

(56) References Cited

U.S. PATENT DOCUMENTS

| | | | | |
|---|---|---|---|---|
| 2017/0213321 | A1* | 7/2017 | Matviychuk | .............. G06T 5/70 |
| 2018/0005111 | A1 | 1/2018 | Chaudhari | |
| 2018/0144465 | A1 | 5/2018 | Hsieh | |
| 2018/0285695 | A1* | 10/2018 | Guo | ....................... G06T 11/008 |
| 2018/0293710 | A1* | 10/2018 | Meyer | ........................ G06T 5/70 |
| 2018/0293711 | A1* | 10/2018 | Vogels | .................... G06F 17/10 |
| 2018/0293713 | A1* | 10/2018 | Vogels | ................... G06V 10/82 |
| 2019/0258917 | A1 | 8/2019 | Chai | |

OTHER PUBLICATIONS

Wang, Z. et.al, "Deep Networks for Image Super-Resolution with Sparse Prior," Proc. ICCV, 2015, p. 9.

Zhang, X., "Thresholding Neural Network for Adaptive Noise Reduction," IEEE Transactions on Neural Networks, vol. 12, No. 3, May 2001, p. 18.

Zhang, K. et.al, "Beyond a Gaussian Denoiser: Residual Learning of Deep CNN for Image Denoising," arXiv: 1608.03981v1, 2016, p. 13.

Wang, Y. et.al, "End-to-End Image Super-Resolution Via Deep and Shallow Convolutional Networks," arXiv: 1607.07680v1, 2016, p. 10.

Kang, E. et al, "A deep convolutional neural network using directional wavelets for low-dose X-ray CT reconstruction," arXiv:16:0.090736v2, 2016, p. 29.

Extended Search Report issued Oct. 8, 2018 in European patent Application No. 18175395.5.

Kenzo Isogawa, et al., "Deep Shrinkage Convolutional Neural Network for Adaptive noise Reduction", IEEE signal Processing Letters, vol. 25, No. 2, Feb. 2018, XP055508221, pp. 224-228.

Dr. Haider Kadiam Hoomod, et al., "Fast Image Denoising Based on Modify CNN and Noise Estimation", Annual Conference on New Trends in Information & Communications Technology Applications—(NTICT'2017) Mar. 7-9, 2017, XP033119162, pp. 280-285.

Szu-Wei Fu, et al., "SNR-Aware Convolutional Neural Network Modeling for Speech Enhancement", Interspeech 2016, vol. 2016, 2016, XP055427533, 6 pages.

Office Action issued Jun. 7, 2022, in corresponding Japanese Patent Application No. 2018-103025, 5 pages.

Japanese Office Action issued Nov. 12, 2024 in Japanese Patent Application No. 2024-008184, 4 pages.

* cited by examiner

ACTIVATION FUNCTION
HARD-SHRINKAGE FUNCTION

ACTIVATION FUNCTION
SOFT-SHRINKAGE FUNCTION

IMAGE PROCESSING SYSTEM AND MEDICAL INFORMATION PROCESSING SYSTEM

CROSS-REFERENCE TO RELATED APPLICATIONS

This application is a division of and claims the benefit of priority under 35 U.S.C. § 120 from U.S. application Ser. No. 18/084,863 filed Dec. 20, 2022, which is a division of U.S. application Ser. No. 15/994,161 filed May 31, 2018 (now U.S. Pat. No. 11,574,170 issued Feb. 7, 2023), and claims the benefit of priority under 35 U.S.C. § 119 from Japanese Patent Application No. 2017-108934 filed Jun. 1, 2017, the entire contents of each of which are incorporated herein by reference.

FIELD

Embodiments described herein relate generally to an image processing system and a medical information processing system.

BACKGROUND

In recent years, a method of using a neural network has been used in the field of various types of image processing and image recognition. The neural network is a processing device in which one or more nodes simulating cells are connected by one or more edges that simulate nerves.

The neural network has biases and weighting coefficients, both of which are associated with respective edges, as its internal parameters. In addition, each node has an activation function, and the parameters of the activation function are also included in the internal parameters of the neural network.

Machine learning is used for calculating the internal parameters of the neural network. For instance, in a neural network aimed at removing noise of an image, the internal parameters are generally calculated in the following manner.

First, initial setting is manually performed on various conditions such as connection relationship between respective nodes, initial values of the biases and weighting coefficients associated with respective edges, and an initial value of the parameter of the activation function in each node.

Next, an image without noise (i.e., a "ground truth") and a "training image" in which noise is artificially superimposed on the ground truth are prepared. The initial parameters of the neural network are sequentially updated in such a manner that the difference between the training image processed in the neural network and the ground truth becomes smaller. Such a series of processing flow is called "training".

When difference, e.g., mean square error (MSE) of each pixel of respective images, between the ground truth and the image obtained by processing the training image in the neural network (i.e., the processed training image) becomes smaller than a predetermined value, the training will end. The respective values of the internal parameters of the neural network at the end of training are held as internal parameters calculated by training.

When using the neural network after the training, a noise-superimposed image in which actual noise is superimposed is inputted to a neural network having internal parameters calculated by the training, and an image in which noise is removed or reduced is obtained at the output of the neural network.

In the neural network, high noise removal performance or noise reduction performance is obtained, when the amount of superimposed noise in the noise-superimposed image to be used is as large as the amount of noise in the training image, which has been used in the training process. However, in the neural network, the noise removal performance or noise reduction performance may deteriorate when the amount of noise in the noise-superimposed image to be used is different from the amount of noise in the training image.

In order to cope with this problem, an approach may be considered in which plural training images, that have noise amounts different from each other, are used when training the internal parameters in the neural network, instead of using training images having a noise amount of a single magnitude. However, in this approach, when assuming the noise amount is same between the leaning process and the using process, the noise removal or noise reduction performance may be reduced, compared with the noise removal or reduction performance obtained by using the training images that have a noise amount of a single magnitude.

DETAILED DESCRIPTION

Hereinafter, respective embodiments of image processing systems will be described with reference to the accompanying drawings. In the embodiments described below, the same reference signs are given for identical components in terms of configuration and function, and duplicate description is omitted.

In one embodiment, an image processing system includes a memory and processing circuitry. The memory is configured to store a predetermined program. The processing circuitry is configured, by executing the predetermined program, to perform processing on an input image by exploiting a neural network having an input layer, an output layer, and an intermediate layer provided between the input layer and the output layer, the input image being inputted to the input layer, and adjust an internal parameter based on data related to the input image, while performing the processing on the input image after training of the neural network, the internal parameter being at least one internal parameter of at least one node included in the intermediate layer, and the input parameter having been calculated by the training of the neural network.

First Embodiment

Figure 1:
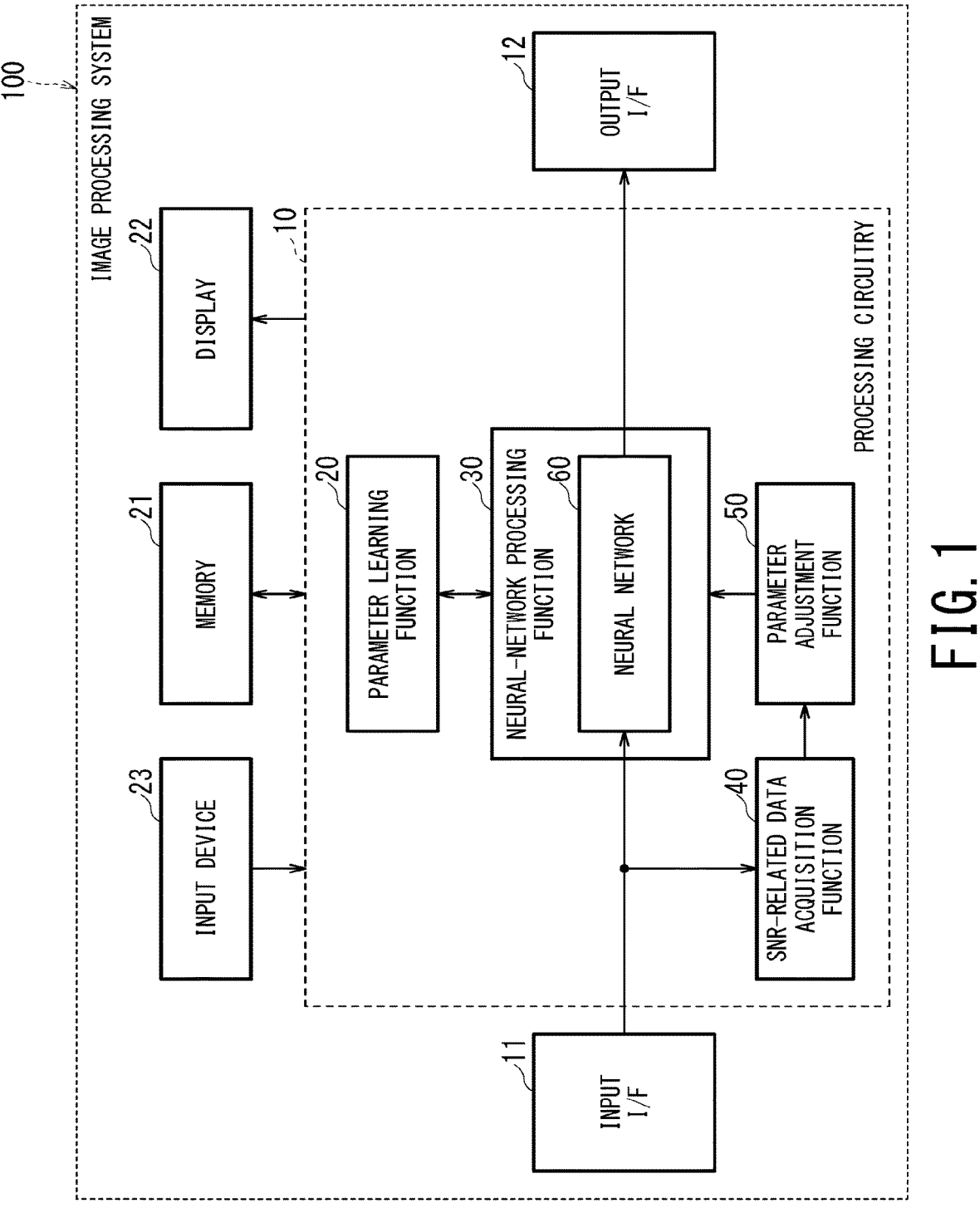
FIG. 1 is a block diagram illustrating a configuration of an image processing system of the first embodiment.

FIG. 1 is a block diagram illustrating an overall configuration of an image processing system 100 according to the first embodiment. The image processing system 100 is constituted by, e.g., a computer system.

As shown in FIG. 1, the image processing system 100 includes processing circuitry 10, an input I/F (interface) 11, an output I/F (interface) 12, memory 21, a display 22, and an input device 23.

The processing circuitry 10 is, e.g., a circuit equipped with a central processing unit (CPU) and/or a special-purpose or general-purpose processor. The processor implements various functions described below by executing programs stored in the memory 21. The processing circuitry may be configured as hardware such as a field programmable gate array (FPGA) or an application specific integrated circuit (ASIC). The various functions described below can also be implemented by such hardware. Additionally, the processing circuitry 10 can implement the various functions by combining hardware processing and software processing based on its processor and programs.

The memory 21 is a recording medium including a read-only memory (ROM), a random access memory (RAM), and an external memory device such as a hard disk drive (HDD) or an optical disc device. The memory 21 stores various programs executed by a processor of the processing circuitry 10 as well as various types of data and information.

The input device 23 includes various devices for an operator to input various types of information and data, and is configured as, e.g., a mouse, a keyboard, a trackball, and/or a touch panel.

The display 22 is a display device such as a liquid crystal display panel, a plasma display panel, and an organic EL panel.

The input I/F 11 and the output I/F 12 are interfaces for inputting and outputting images, respectively. Each of the input I/F 11 and the output I/F 12 may include various devices and circuits such as a wired or wireless LAN, various communication interfaces including a USB, a network interface including the Internet and a public telephone line, and a drive circuit of various storage media including an optical disk and a magnetic disk. By using these devices and circuits, the input I/F 11 and the output I/F 12 can input and output image data, respectively.

As shown in FIG. 1, the processing circuitry 10 implements a parameter learning function 20, a neural-network processing function 30, an SNR-related data acquisition function 40, and a parameter adjustment function 50 by, e.g., executing various programs stored in the memory 21.

The parameter learning function 20 determines respective values of internal parameters of the neural network 60 by machine learning (hereinafter, simply referred to as learning) with the use of a training image, as described below.

The neural-network processing function 30 performs a predetermined processing on the input image inputted to the neural network 60 after training, by using the neural network 60.

The SNR-related data acquisition function 40 acquires at least one of signal strength of the input image, magnitude of noise in the input image, signal-to-noise ratio (SNR) of the input image, gain used in normalization processing, data related to the signal-to-noise ratio, from the input image or supplementary information of the input image (hereinafter, the data acquired by the SNR-related data acquisition function are referred to as "SNR-related data"). Note that the SNR-related data are data related to the input image.

The parameter adjustment function 50 adjusts the respective values of the internal parameters of the neural network 60 on the basis of the SNR-related data acquired by the SNR-related data acquisition function 40, when the neural-network processing function 30 performs the predetermined processing on the input image inputted to the neural network 60 after training.

As to the parameter learning function 20, the neural-network processing function 30, the SNR-related data acquisition function 40, and the parameter adjustment function 50, their details will be described below.

Figure 2:
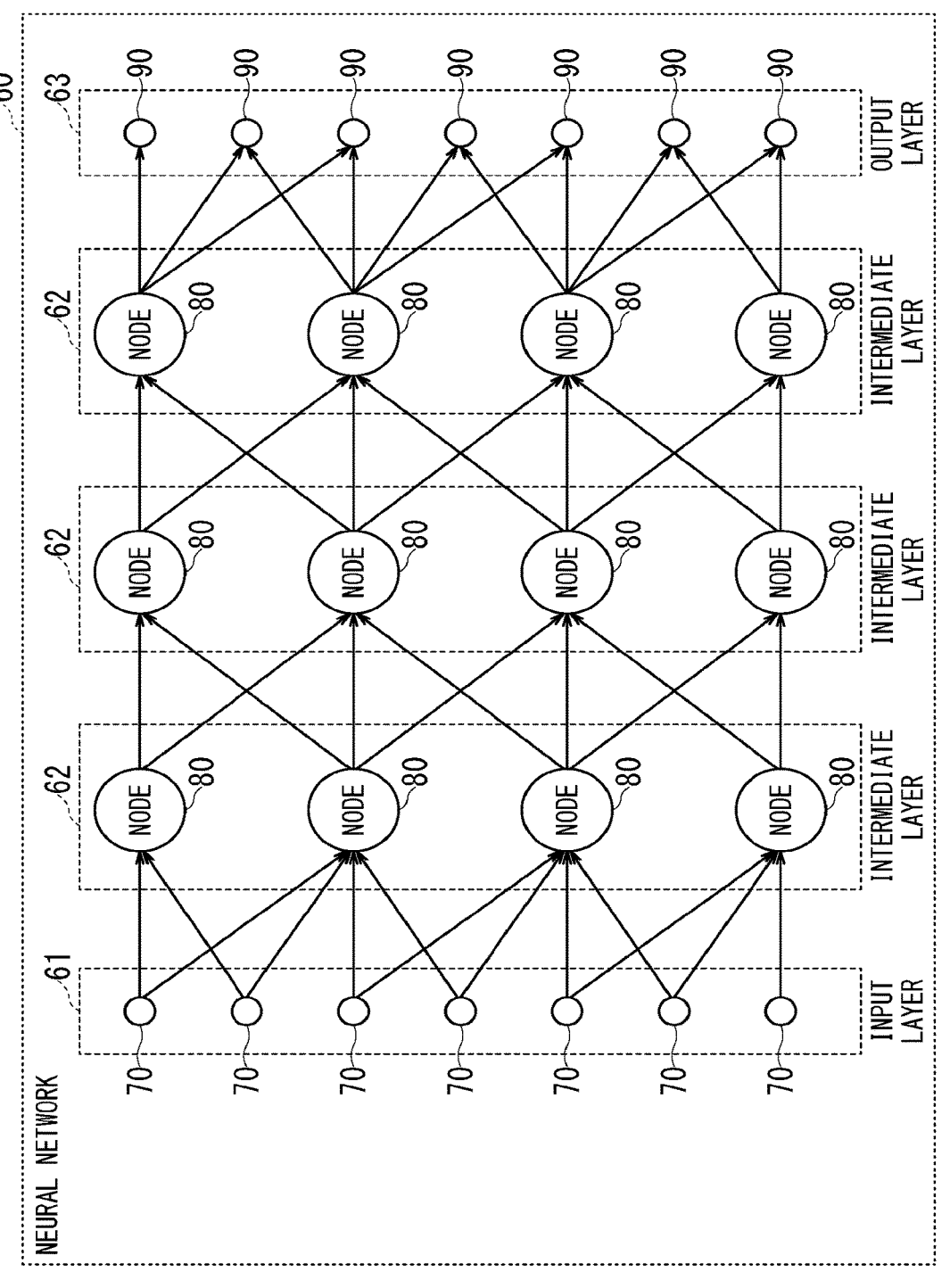
FIG. 2 is a schematic diagram illustrating an internal configuration of a neural network in which a configuration capable of adjusting internal parameters is omitted.

FIG. 2 is a schematic diagram illustrating an internal configuration of the neural network 60. Although the internal parameters are adjustable in the image processing system 100 according to the first embodiment, FIG. 2 illustrates only the basic configuration for avoiding complication and omits the configuration portion that can adjust the internal parameters.

As shown in FIG. 2, the neural network 60 has a multilayer structure that includes an input layer 61, an output layer 63, and at least one intermediate layer 62 between the input layer 61 and the output layer 63.

The input layer 61 includes plural input terminals 70. The image processing system 100 of the present embodiment performs image processing such as noise reduction processing or noise removal processing by using the neural network 60. In this case, image data are inputted to the input layer 61. Further, for instance, pixel signals constituting image data are inputted to the respective input terminals 70 of the input layer 61.

The output layer 63 also has plural output terminals 90. In the image processing system 100 of the present embodiment, the image data subjected to the image processing are outputted from the output layer 63. For instance, pixel signals of the image data subjected to the image processing are outputted to the respective output terminals 90 of the output layer 63.

Each of the intermediate layers 62 includes plural nodes 80. Focusing on one intermediate layer 62 between other intermediate layers 62, the output signals of the plural nodes 80 of the immediately preceding intermediate layer 62 are inputted to each node 80 of the focused intermediate layer 62, and an output signal of each node 80 of the focused intermediate layer 62 is distributed to plural nodes 80 of the immediately subsequent intermediate layer 62.

When the intermediate layer 62 is immediately subsequent to the input layer 61, plural signals of the respective plural input terminals 70 are inputted to each node 80 of this intermediate layer 62, and each of the plural signals are outputted to the nodes 80 of the intermediate layer 62 of the subsequent stage.

When the intermediate layer 62 is immediately prior to the output layer 63, output signals of the respective nodes 80 of this intermediate layer 62 are outputted to the output terminals 90 of the output layer 63

Figure 3:
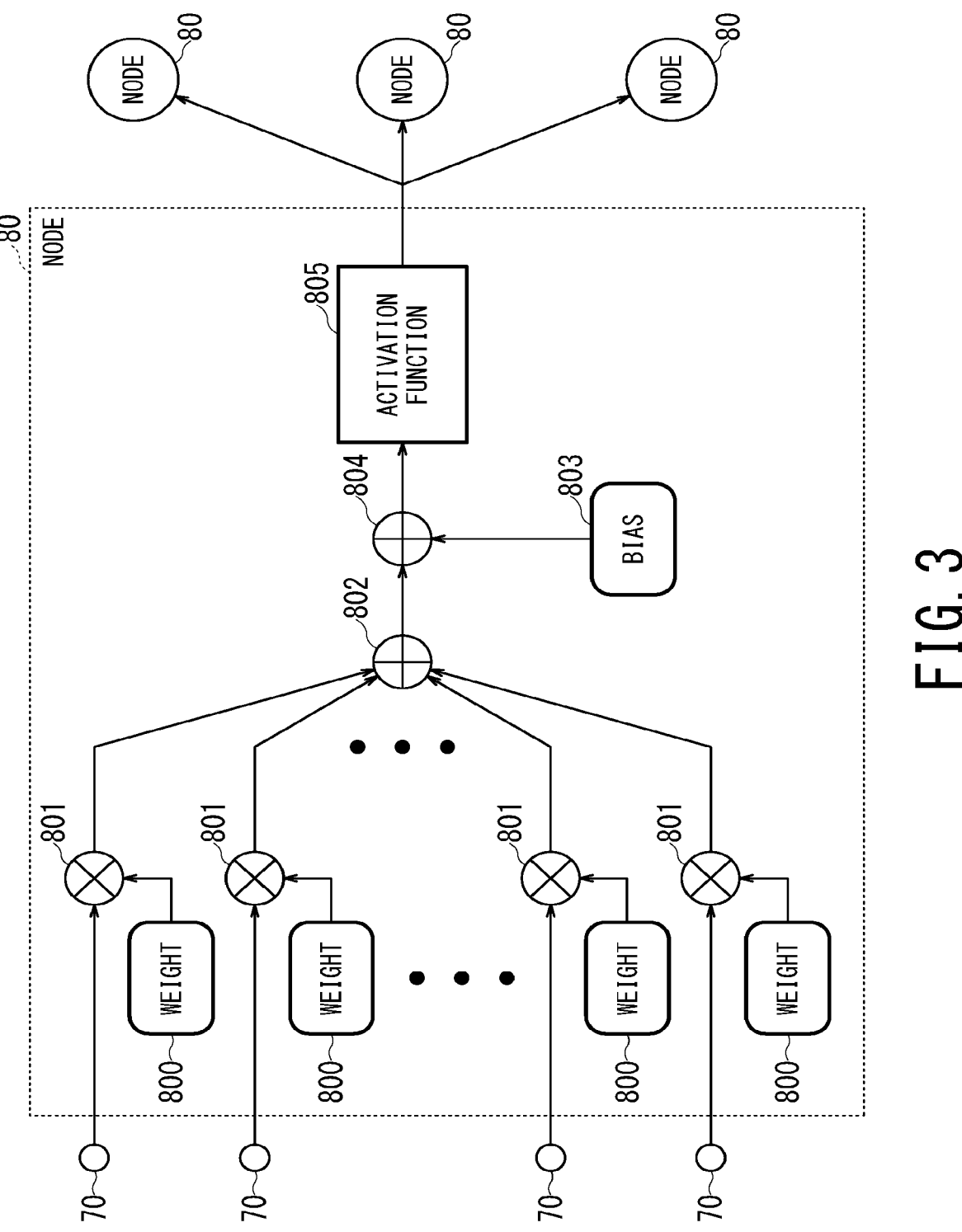
FIG. 3 is a schematic diagram illustrating an internal configuration of a node in which a configuration capable of adjusting internal parameters is omitted.

FIG. 3 is a schematic diagram illustrating an internal configuration of the node 80. Although FIG. 3 illustrates a node 80 in the intermediate layer 62 that is immediately subsequent to the input layer 61, other nodes in the intermediate layer 62 may have the same configuration. Plural signals are inputted to the node 80 shown in FIG. 3. Respective input signals are subjected to weighting with weights 800 through the multipliers 801, and then summed up by an adder 802. Further, an adder 804 adds a bias 803 to the output of the adder, and then, the output of the adder 804 is sent to the activation function 805. When the output of adder 804 is defined as "x", "x" is expressed by the following equation (1).

$$x = \left( \sum_i w_i s_i \right) + b \qquad \text{Equation (1)}$$

In the equation (1), "$w_i$" is the weight 800, "$s_i$" is the input signal, "i" is the number of the input signal, and "b" is the bias 803.

By applying the activation function 805 to "x" in the equation (1), the output of the node 80 is determined. Various subdifferentiable functions, such as a clipping function expressed by the equation (2), a ReLU function expressed by the equation (3), or a tank function expressed by the equation (4), have been conventionally used.

$$f_{clip}(x, U, L) = \begin{cases} U & (x > U) \\ L & (x < L), x \in R, U \in R, L \in R \\ x & \text{otherwise} \end{cases} \qquad \text{Equation (2)}$$

$$f_{ReLU}(x) = \begin{cases} 0 & (x < 0) \\ x & \text{otherwise} \end{cases} \qquad \text{Equation (3)}$$

$$\tanh(x) = \frac{e^x - e^{-x}}{e^x + e^{-x}} \qquad \text{Equation (4)}$$

In the present embodiment, for instance, the Soft-Shrinkage function expressed by the following equation (5) may be used as the activation function 805. The Soft-Shrinkage function will be described below.

$$f_{SS}(x, T) = \begin{cases} x - T & (x > T) \\ x + T & (x < -T), T \ge 0 \\ 0 & \text{otherwise} \end{cases} \qquad \text{Equation (5)}$$

In addition, the internal parameters of the conventional neural network 60 are determined by learning performed in advance. Then, when exploiting the neural network 60, i.e., when using the neural network 60, the respective determined values of the internal parameters are used in a fixed state.

By contrast, in the present embodiment, the respective values of the internal parameters of the neural network 60 can be adjusted on the basis of data related to the input image, when predetermined processing is performed after training, i.e., when the neural network 60 is exploited after training.

Figure 4:
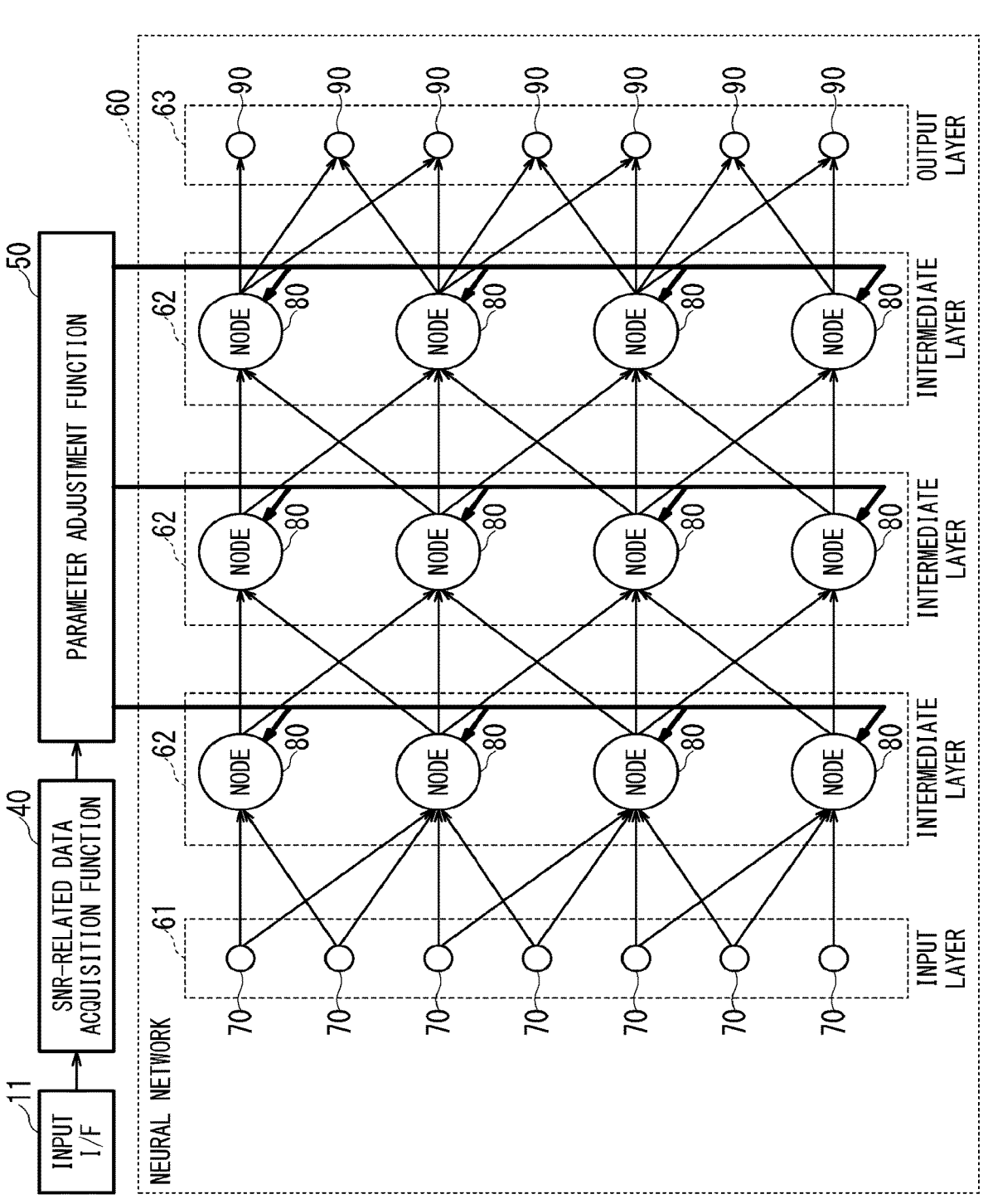
FIG. 4 is a schematic diagram illustrating connection relationship between (a) the neural network of the present embodiment having a configuration capable of adjusting internal parameters and (b) an SNR-related data acquisition function and a parameter adjustment function, both of which provides a control signal to the neural network.

FIG. 4 is a schematic diagram illustrating connection relationship between (a) the neural network 60 of the present embodiment configured to be able to adjust the internal parameters and (b) the parameter adjustment function 50 and the SNR-related data acquisition function 40 providing a control signal to the neural network 60.

The parameter adjustment function 50 supplies the control signal to at least some nodes 80 of the intermediate layers 62. For instance, the parameter adjustment function 50 supplies a control signal to the nodes 80 of at least one intermediate layer 62. As shown in FIG. 4, the control signal may be supplied from the parameter adjustment function 50 to each node 80 of the intermediate layers 62.

Figure 5:
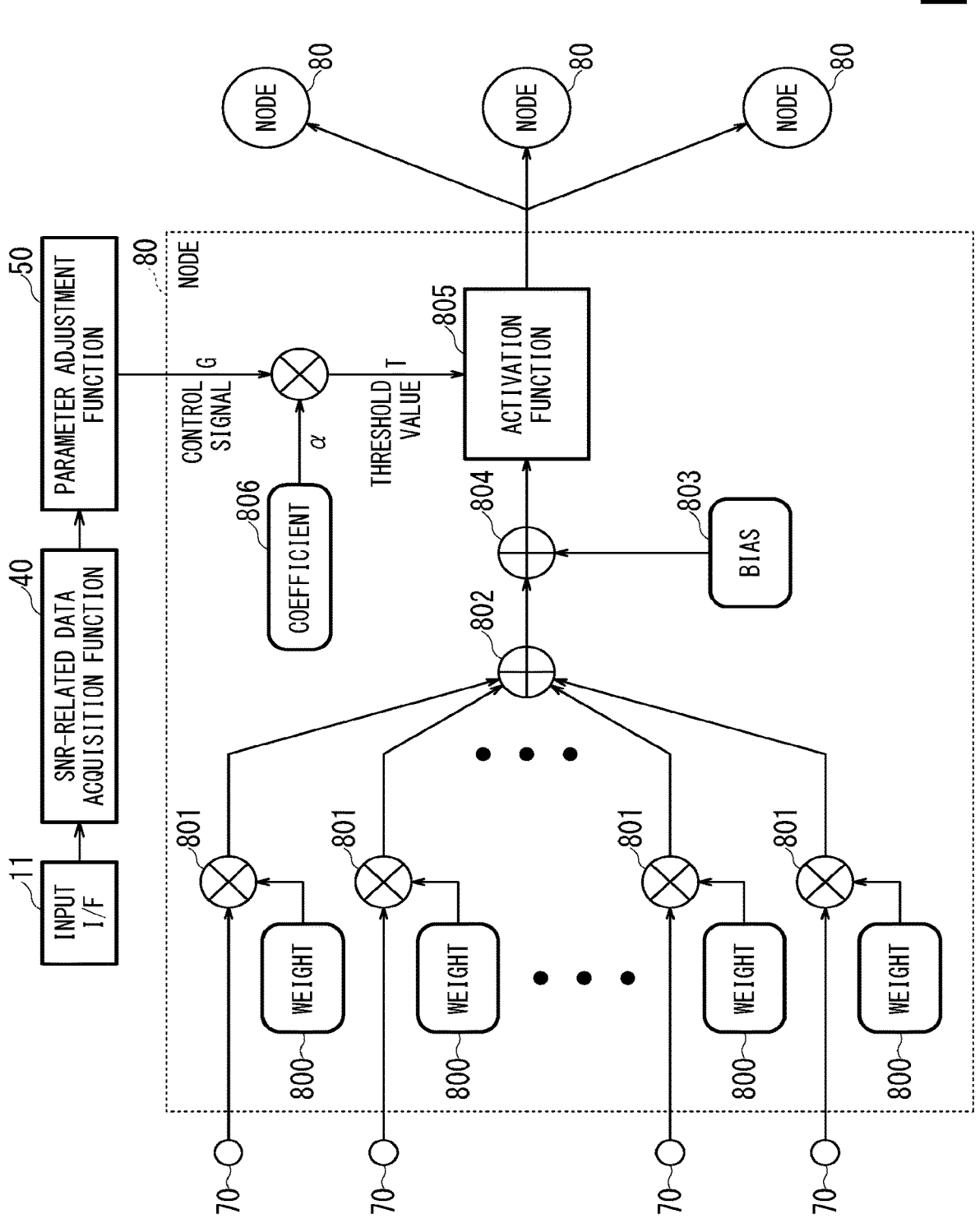
FIG. 5 is a block diagram illustrating an internal configuration of one node of the present embodiment.

FIG. 5 is a block diagram illustrating an internal configuration of one node 80 of the present embodiment. The node 80 shown in FIG. 5 is configured such that threshold T, which is the parameter of the activation function 805 (i.e., one of the internal parameters of the node 80), is adjusted with respect to the activation function 805.

Figures 6A, 6B:
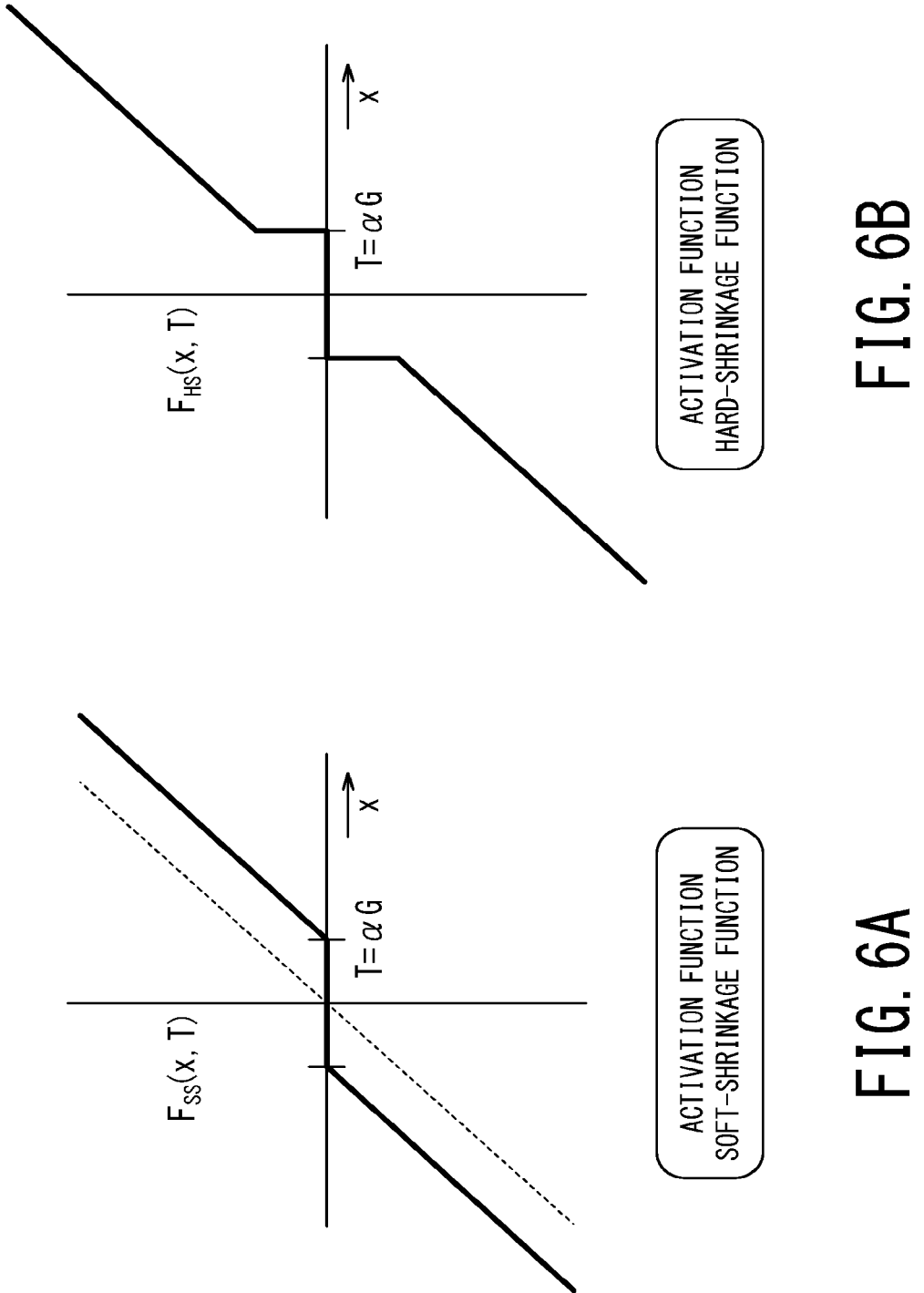
FIG. 6A is a graph illustrating the Soft-Shrinkage function $F_{SS}$ (x, T) as one case of an activation function used in the present embodiment.
FIG. 6B is a graph illustrating the Hard-Shrinkage function $F_{HS}$ (x, T) as one case of an activation function used in the present embodiment.

FIG. 6A is a graph illustrating a Soft-shrinkage function $F_{SS}(x, T)$ as an example of the activation function 805 in which the threshold T is used as a parameter. Similarly, FIG. 6B is a graph illustrating a Hard-Shrinkage function $F_{HS}(x, T)$ as an example of the activation function 805 in which the threshold T is used as a parameter. Each of the Soft-Shrinkage function $F_{SS}(x, T)$ and the Hard-Shrinkage function $F_{HS}(x, T)$ is a function that outputs zero when an input value lies within a predetermined positive/negative threshold ±T around zero, and outputs a value proportional to an input value when an input value lies outside the range of the threshold ±T.

Note that, when the input is out of the range of the threshold ±T, the amplitude of the output of the Soft-Shrinkage function $F_{SS}(x, T)$ becomes smaller than the amplitude "x" of the input by the threshold T. Meanwhile, the amplitude of the output of the Hard-Shrinkage function $F_{HS}(X, T)$ has the same value as the amplitude "x" of the input, when the input is out of the range of the threshold ±T, By using the Soft-Shrinkage function $F_{SS}(x, T)$ or the Hard-Shrinkage function $F_{HS}(x, T)$ as the activation function 805, a signal with amplitude smaller than the threshold value T, i.e., a weak signal, which most likely be a noise, can be made zero at the output of the activation function.

As described above, the neural network 60, which uses the Soft-Shrinkage function $F_{SS}(x, T)$ or the Hard-Shrinkage function $F_{HS}$ (x, T) as the activation function 805, is a technology for reducing noise in an image and exerts a noise reduction effect when the threshold value T is set to an appropriate magnitude with respect to the noise level.

As shown in FIG. 5, the threshold value T can be determined by, e.g., T=αG as the product of the coefficient α, which is the internal parameter, and the control signal G, which comes from the outside. For instance, the SNR-related data acquisition function 40 acquires data related to SNR or magnitude of noise of the input image (i.e., SNR-related data) from the input image (or from its supplementary information) inputted via the input I/F 11, and outputs the acquired SNR-related data to the parameter adjustment function 50. Further, the parameter adjustment function 50 determines magnitude of the control signal G on the basis of the SNR-related data and supplies the control signal G to each node 80. For instance, when the SNR-related data indicates that SNR of the input image is low or noise included in the input image is large, the parameter adjustment function 50 sets the control signal G to be a large value and supplies it to each of the nodes 80.

The image processing system 100 of the present embodiment is a system that exploits the neural network 60. Thus, the image processing system 100 has "a learning mode" for causing the neural network 60 to learn and "an image processing mode" for performing image processing by exploiting the neural network 60 after the training performed by the neural network 60.

Figure 7:
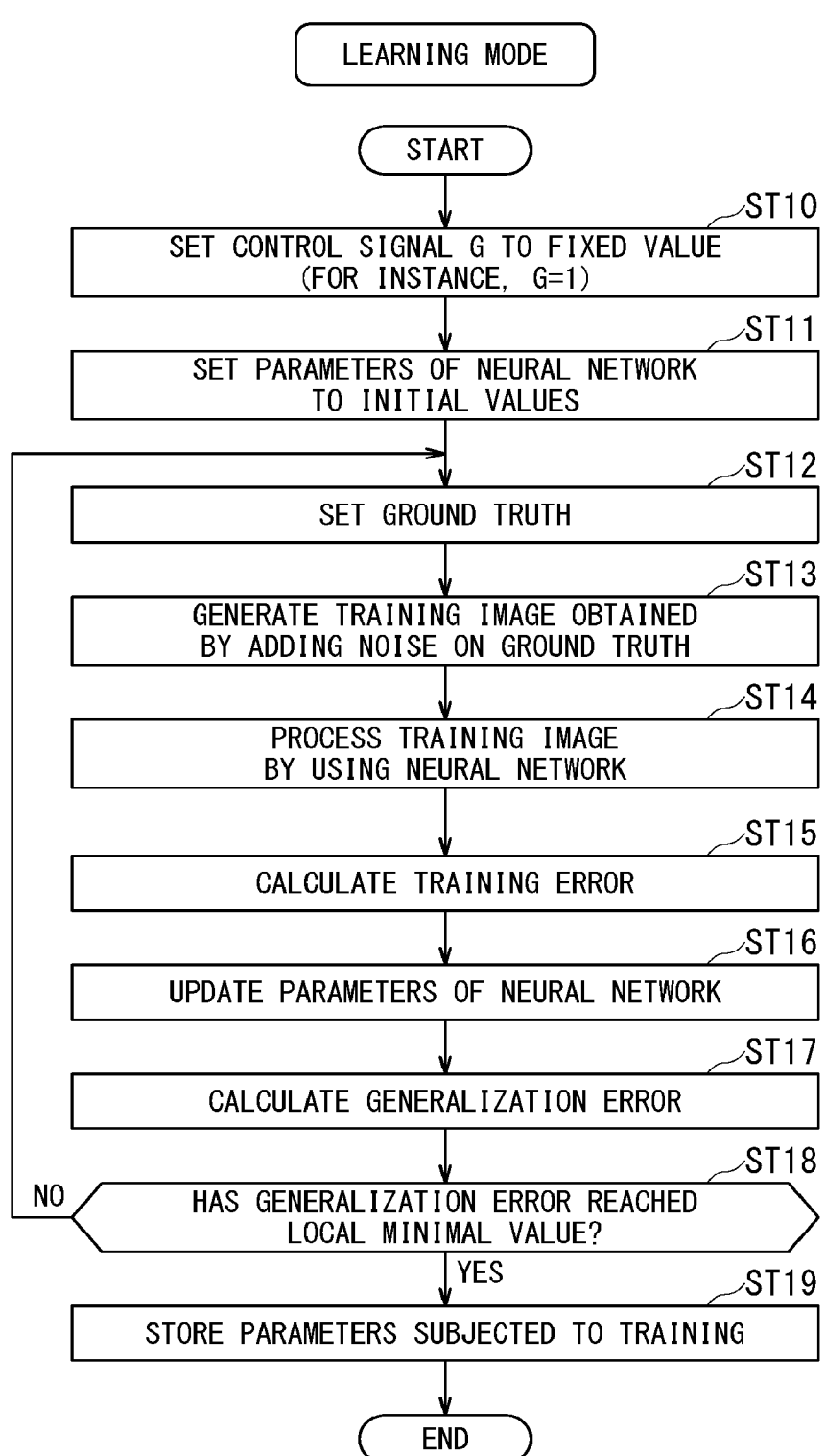
FIG. 7 is a flowchart illustrating an operation of a learning mode.

FIG. 7 is a flowchart illustrating an operation of the learning mode of the image processing system 100, out of the above-described two operation modes.

First, in the step ST10, the control signal G from the outside to the neural network 60 is set to a fixed value. The control signal G shown in FIG. 5 is fixed to, e.g., G=1.

In the next step ST11, the respective values of the internal parameters of the neural network 60 are set to initial values (i.e., default values). For instance, the respective values of the internal parameters such as the value of the weight 800 in each node 80, the value of the bias 803, and the value of the coefficient α shown in FIG. 5 are set to the initial values.

In the next step ST12, a ground truth IM is set. The image processing system 100 according to the present embodiment performs processing for removing or reducing noise included in an input image. Thus, an image with no noise or an image with a very high SNR is selected as the ground truth IM, and this ground truth IM is set as preparation for training in the neural network 60.

In the next step ST13, a training image obtained by adding artificial noise to the ground truth is generated, and similarly, this training image is set as preparations for training in the neural network 60. The artificial noise is, e.g., Gaussian noise that is generated by calculation so as to have a standard deviation σ of a predetermined magnitude, and the training image is generated by adding this artificial noise to each pixel value of the ground truth.

In the next step ST14, the generated training image is inputted to the neural network 60, and its processing result is obtained.

For instance, the pixel values of the respective pixels of the training image, to which noise is added, are inputted to the respective input terminals 70 of the input layer 61 of the neural network 60. These pixel values propagate each node 80 of the intermediate layers 62 of the neural network 60 from the input layer 61 to the output layer 63 while changing their values by being subjected to weighted addition, bias addition, and activation function processing shown in FIG.

5, and then outputted to the output terminals 90 of the output layer 63 as the pixel values of the image processed by the neural network 60.

In next step ST15, an error (i.e., training error) between the processed image and the ground truth is calculated. Specifically, as the training error, it is possible to use the mean square error (MSE) and the sum of square errors, both of which can be obtained from each pixel of the processed image and each pixel of the ground truth.

In the next step ST16, the parameters of the neural network are updated such that the training error becomes smaller by using the error back propagation algorithm. In particular, the algorithms stated in the following Document 1 and Document 2 can be used for updating the parameters of the Shrinkage function.

[Document 1] Z. Wang et. al, "Deep Networks for Image Super Resolution with Sparse Prior," Proc. ICCV2015.

[Document 2] X. Zhang, "Thresholding Neural Network for Adaptive Noise Reduction," IEEE Transactions on Neural Networks, vol. 12, no. 3, 2001.

In the next step ST17, by using the correct image that is an image having a high SNR prepared separately from the ground truth and a verification image obtained by adding noise to the correct image, the parameter learning function calculates an error (generalization error) between the correct image and an image obtained by processing the verification image, using the neural network 60.

In the next step ST18, it is determined whether the generalization error has reached the local minimum value or not, and the parameter updating is completed when the generalization error reaches the local minimum value. Conversely, when the generalization error does not reach the local minimum value, the processing returns to the step ST12 and the processing is repeated from the step ST12.

Figure 8:
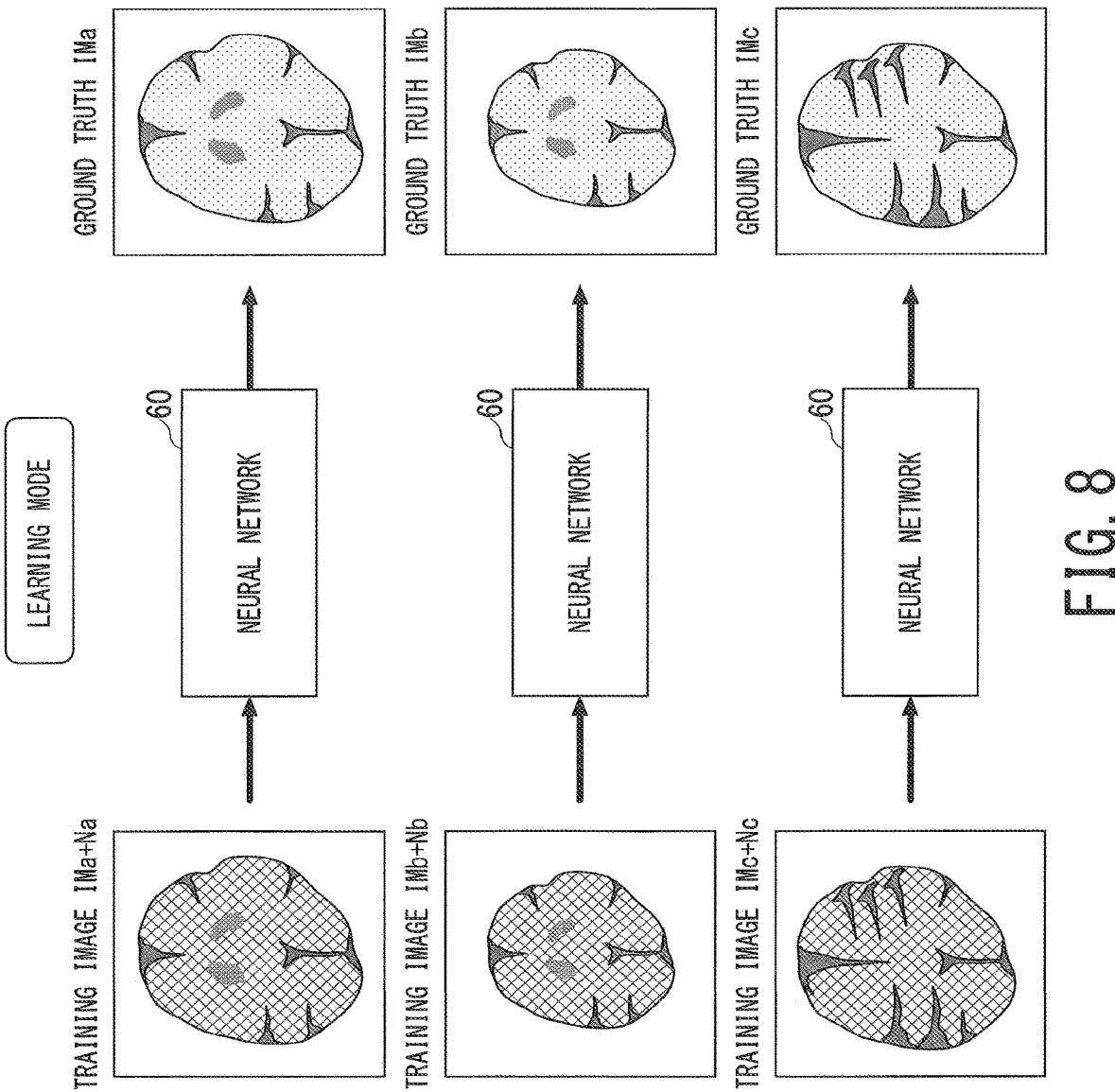
FIG. 8 is a schematic diagram illustrating processing of a learning mode in which a ground truth and a training image are used.

FIG. 8 is a schematic diagram illustrating the above-described processing. As shown in the upper part of FIG. 8, the ground truth IMa having no noise or a very high SNR is set on the output side of the neural network 60. In addition, a training image obtained by adding artificial noise Na to this ground truth IMa is inputted to the neural network 60. Then, the internal parameters of the neural network 60 are determined in such a manner that the training image processed by the neural network 60 approaches the ground truth. The process of determining these internal parameters is a process called machine learning or simply learning.

Although the number of the ground truth(s) used for training may be one, the training effect can be improved by causing the neural network 60 to learn by using plural similar different ground truth. For instance, as shown in the middle part and the bottom part of FIG. 8, the training effect can be enhanced by training with plural images in which the combination of the ground truth IMb and the training image IMb+Nb, and/or the combination of the ground truth IMc and the training image IMc+Nc are used in addition to the combination of the ground truth IMa and the training image IMa+Na.

In the case of training with the use of plural ground truth, first, the steps ST12 to ST18 in the flowchart of FIG. 7 are executed for selected one of the plural ground truth. In this case, when it is determined that the generalization error has not reached the local minimum value for this selected ground truth in the step ST18, the processing returns to the step ST12, in which the ground truth is replaced by a new ground truth (i.e., another of the plural ground truth) so that the processing from the steps ST13 to ST18 is executed for the replaced new ground truth.

When training of all the ground truth has been completed, the internal parameters of the neural network 60 after the training are stored in the memory 21 in the step ST19. Alternatively or additionally, information regarding the structure of the neural network 60 may be stored in the memory 21. That is, assuming that the structure of the neural network 60 and the internal parameters are referred to as a machine learning model, in the step ST19, the entire machine learning model after training may be stored.

Each process of the above-described learning mode is performed by the parameter learning function 20 in FIG. 1.

Figure 9:
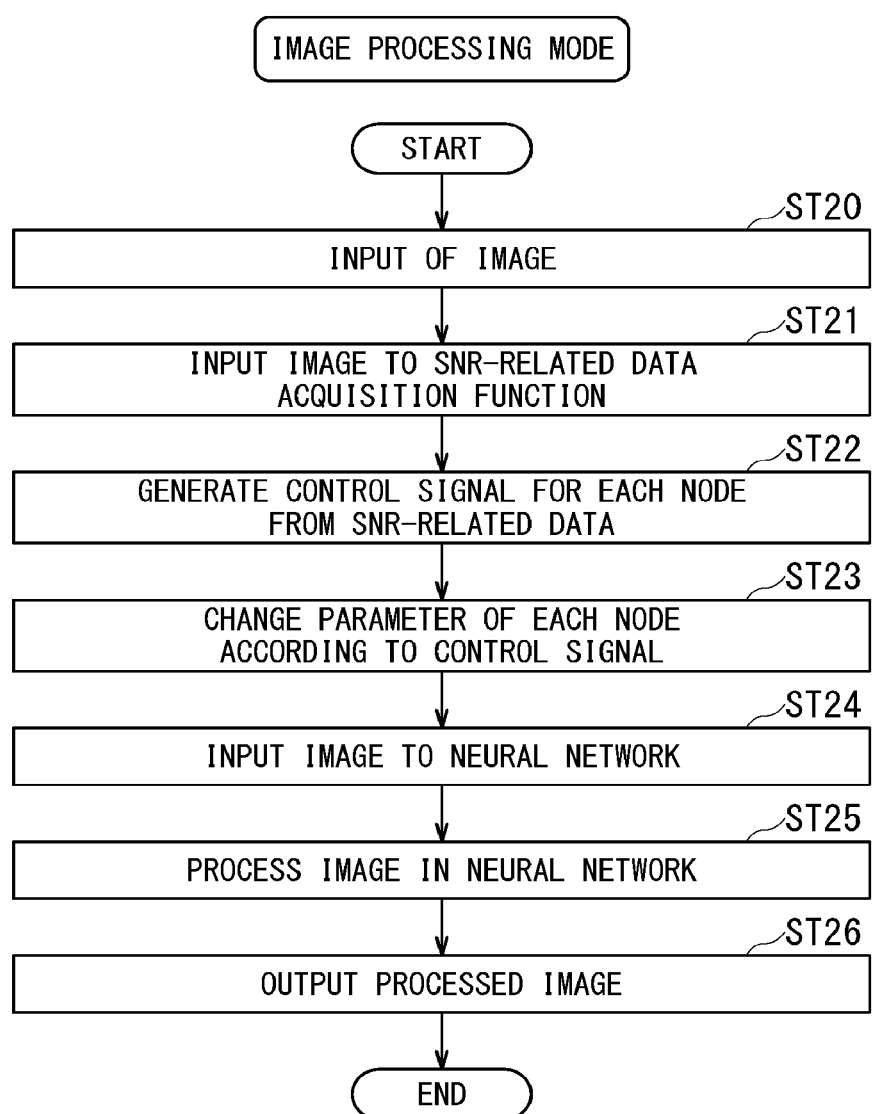
FIG. 9 is a flowchart illustrating processing of an image processing mode, after training performed by a neural network.

FIG. 9 is a flowchart illustrating processing of the image processing mode of the image processing system 100, i.e., an operation mode at the time of exploiting the neural network 60 after completion of training by the neural network 60.

In the first step ST20, an image is inputted to the processing circuitry 10 via the input I/F 11. Specifically, an image is inputted to the SNR-related data acquisition function 40. The image to be inputted is an image to be subjected to noise removal processing or noise reduction processing with the use of the neural network 60. For instance, the input image is an image imaged by a medical image diagnostic apparatus such as an MRI (magnetic resonance imaging) apparatus, a CT (computerized tomography) apparatus, and an ultrasonic diagnostic apparatus. The SNR-related data are attached to this image.

In the next step ST21, the SNR-related data acquisition function 40 acquires the SNR-related data from the input image.

In the next step ST22, the parameter adjustment function 50 generates the control signal for each of the nodes 80 of the neural network 60 from the SNR-related data. There are various specific methods to acquire the SNR-related data from an input image to generate the control signal.

Figure 10:
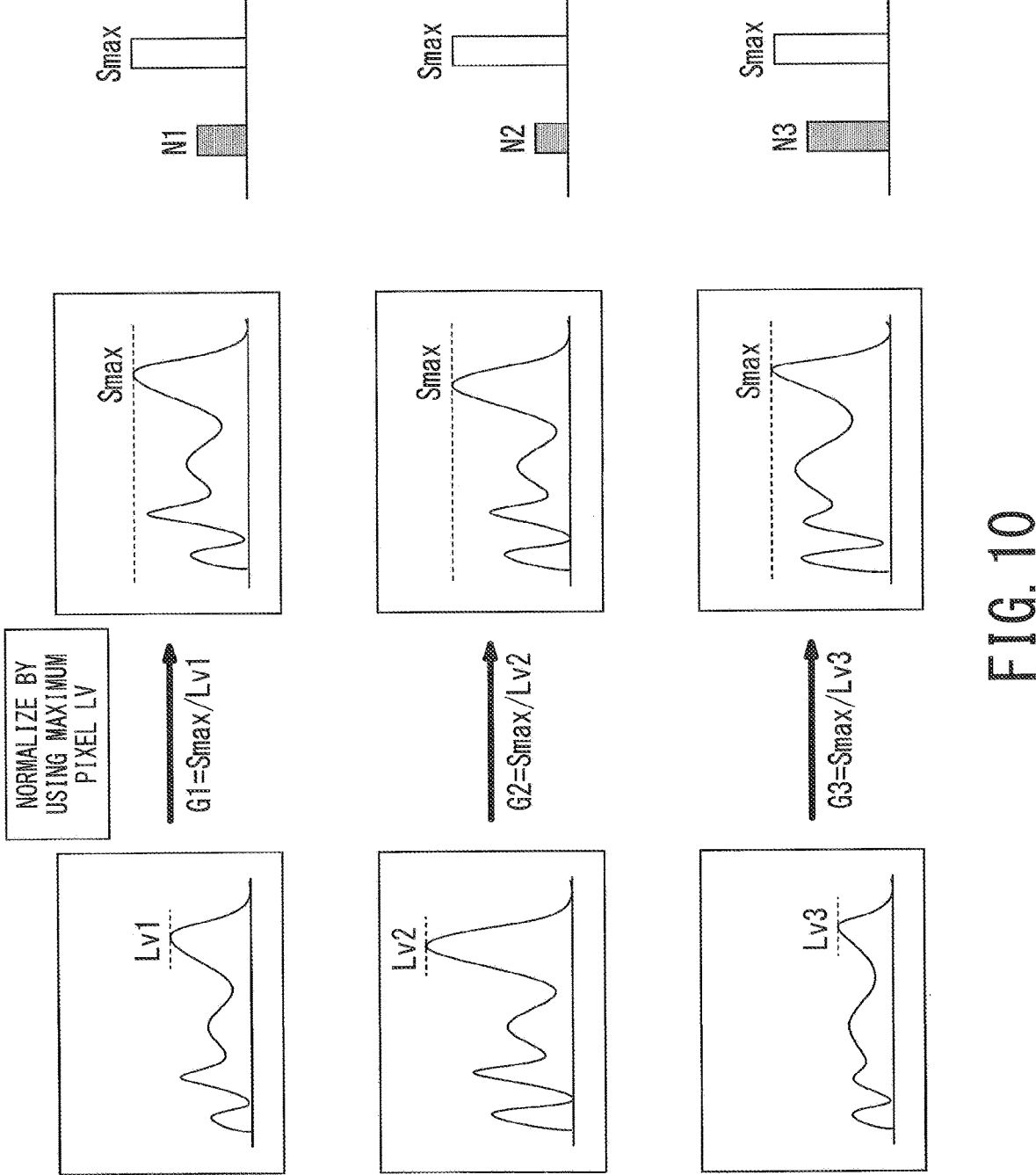
FIG. 10 is a schematic diagram illustrating a normalization process using a maximum pixel value and a calculation method of a control signal.

FIG. 10 is a schematic diagram illustrating a method of calculating the control signal G, when normalization of each pixel value by using the maximum pixel value Lv in the image is performed before the noise removal processing or noise reduction processing by the neural network 60.

When such normalization processing is performed, the SNR-related data acquired by the SNR-related data acquisition function 40 correspond to the maximum pixel value Lv in the image. For instance, as shown in the left column of FIG. 10, it is assumed that processing targets are three types of images and the respective maximum pixel values Lv of these three types of images are Lv1, Lv2, and Lv3, which are different from each other (Lv2>Lv1>Lv3). In this case, in order to make the maximum pixel values after normalization to become Smax, each pixel of respective three images is needed to be multiplied by the respective gains of G1=Smax/Lv1, G2=Smax/Lv2, and G3=Smax/Lv3.

Usually, the magnitude (e.g., rms value of noise) of noise of an image at the time of imaging (i.e., noise of the image before normalization) is common between images. Thus, when normalization is performed with respect to the maximum pixel value Lv in the image, the magnitude N of the normalized noise differs for each image, as shown in the right column of FIG. 10 (N2<N1<N3). By providing the gain G used for the normalization to the neural network 60 as the control signal, it is possible to provide the neural network 60 with data that have correlation with the magnitude of the noise of the processing target image.

Returning to FIG. 9, in the next step ST23, the internal parameters of the respective nodes are adjusted in accordance with the control signal provided from the parameter adjustment function 50.

Figures 11A, 11B, 11C:
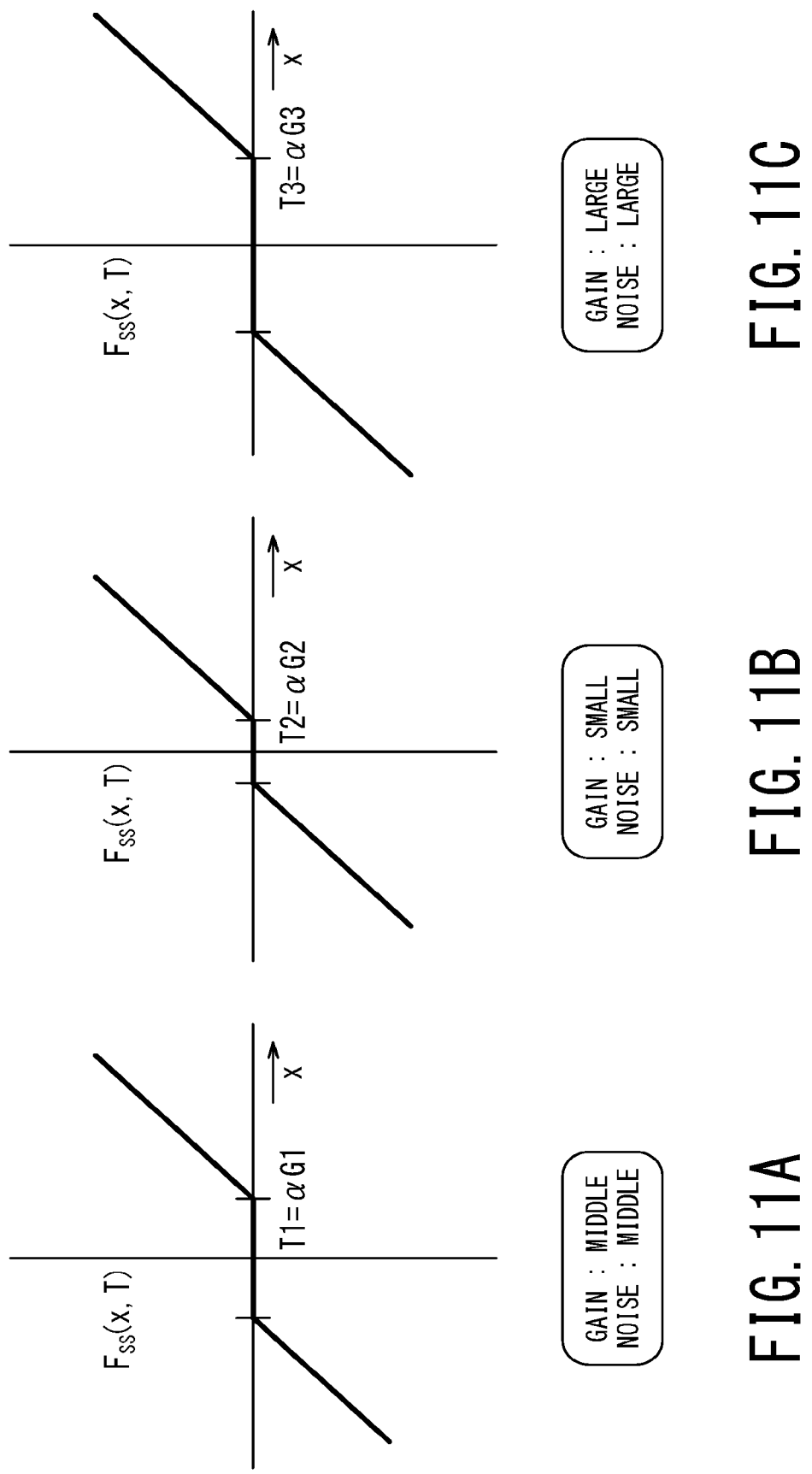
FIG. 11A to FIG. 11C are schematic diagrams illustrating a case where a threshold value T of the Soft-Shrinkage function as an activation function is adjusted by the control signal G.

FIG. 11A to FIG. 11C are schematic diagrams illustrating a case where the internal parameter adjusted in the step ST23 is the threshold value T of the Soft-Shrinkage function. Specifically, FIG. 11A illustrates a case where the activation function 805 is the Soft-Shrinkage function expressed by the equation (5) and the threshold T of the Soft-Shrinkage function is adjusted by the control signal G so as to become T1=αG1. Similarly, FIG. 11B and FIG. 11C illustrate cases where the activation function 805 is the same Soft-Shrinkage function and the threshold T of the Soft-Shrinkage function is adjusted by the control signal G so as to become T2=AG2 and T3=aG3, respectively.

As the gain G (i.e., magnitude of noise) increases, the width of the input at which the output becomes zero also increases, and the effect of removing or reducing noise is maintained, independent of the magnitude of the noise.

In the next step ST24, the image inputted to the input I/F 11 is inputted to the neural network 60.

In the next step ST25, the image inputted to the neural network 60 is processed in the neural network 60.

In the next step ST26, the image processed in the neural network 60 is outputted from the output I/F 12.

Figure 12:
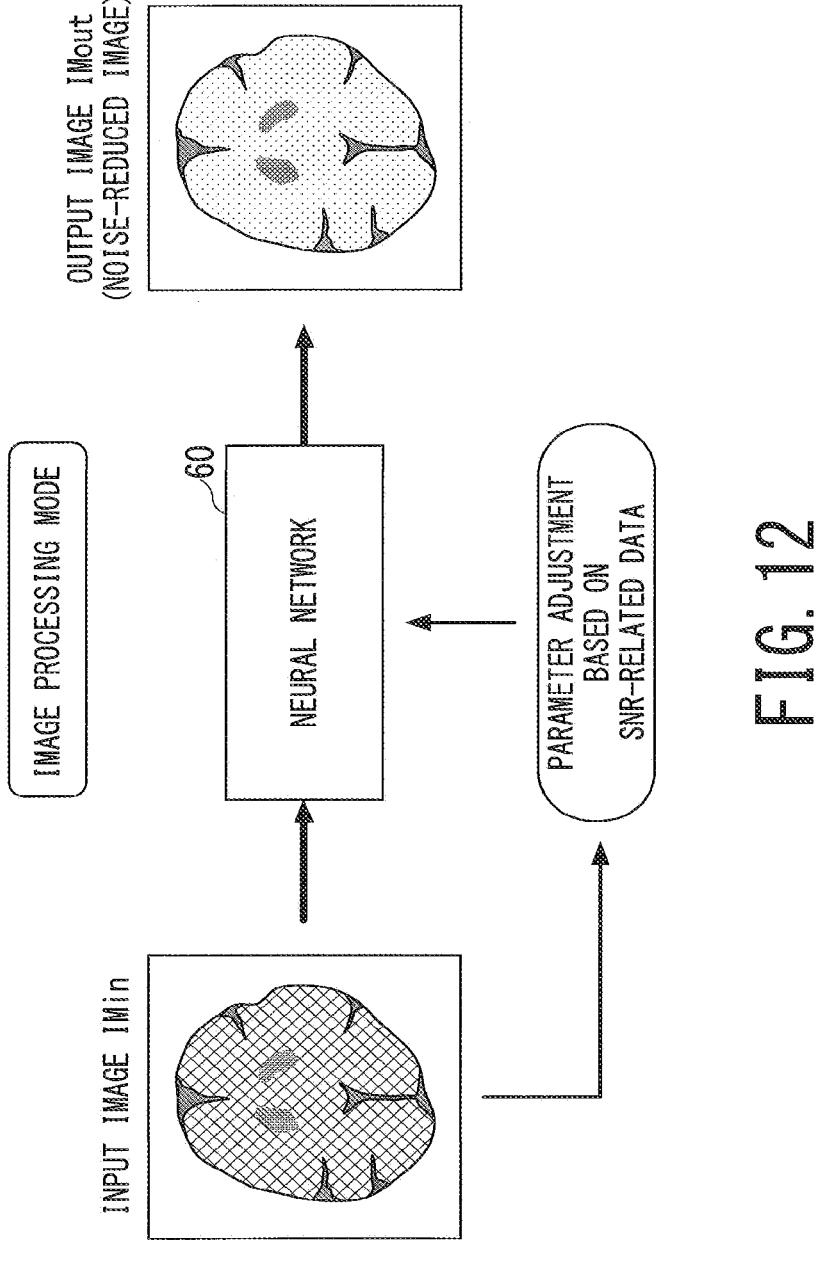
FIG. 12 is a schematic diagram illustrating an operation concept of a neural network according to the present embodiment in the image processing mode.

FIG. 12 is a schematic diagram illustrating the operation concept of the neural network 60 of the present embodiment in the image processing mode. The image processing system 100 of the present embodiment has a function of acquiring the SNR-related data from the input image IMin of the neural network 60 and adjusting the parameters of the neural network 60 on the basis of the acquired SNR-related data.

Conventional neural networks have the problem that the effect of removing or reducing noise decreases when magnitude of noise included in the image used in the learning mode is different in magnitude of noise included in the image in the image processing mode after the training.

However, even after training of the neural network 60, the image processing system 100 according to the present embodiment has a function of adjusting the parameters of the neural network 60 depending on the magnitude of noise included in the image that is inputted in the image processing mode. As a result, even when magnitude of noise included in the image used in the learning mode is different in magnitude of noise included in the image inputted in the image processing mode after training, it is possible to maintain the effect of removing or reducing noise.

The SNR-related data are not limited to the gain G used for normalizing an image with the maximum pixel value, as mentioned above. Hereinafter, some other examples of the SNR-related data will be described.

For instance, when the image to be processed is an image imaged by a camera, the SNR-related data acquisition function 40 may acquire an F-value and/or an exposure time of the camera at the time of imaging as the SNR-related data from, e.g., supplementary information of the camera image. This is because the F value and the exposure time influence the number of photons made incident on the pixels of the image sensor and the shot noise decreases as the number of photons increases.

For instance, when the image to be processed is a medical image generated by an MRI apparatus, the SNR-related data acquisition function 40 may acquire one or more combinations of parameters related to imaging conditions from the MRI apparatus as the SNR-related data. The parameters related to imaging conditions are, e.g., number of phase encoding steps Ny, number of frequency encoding steps Nx, voxel volume ($\Delta x \Delta y \Delta z$), bandwidth Bw, and number of times of integration Nex. This is because SNR of a medical image generated by an MRI apparatus is expressed by the following expression.

$$SNR \propto \Delta x \Delta y \Delta z \sqrt{\frac{N_x N_y N_{ex}}{B_w}}$$

Further, for instance, when the image to be processed is a medical image generated by a CT apparatus, the SNR-related data acquisition function 40 may acquire at least one of tube voltage, tube current, irradiation time, object size, exposure dose, and/or the number of beams, from the CT apparatus as the SNR-related data. This is because these parameters correlate with SNR and noise amount of a medical image generated by a CT apparatus.

In addition, when the image to be processed is a radar image, the SNR-related data acquisition function 40 may acquire the magnitude of the received signal and/or the gain of the signal receiver as the SNR-related data.

Further, in the case of using a signal value such as Lv for adjusting the threshold value T of the Soft-Shrinkage function, there is a possibility that the processing performance may deteriorate when dynamic range of the signal changes. For instance, consider a case where training is completed by using data of an input image in which dynamic range of each pixel value corresponds to 8 bit, while the processing circuitry 10 is connected to an image sensor (e.g., a camera) configured to generate image data in which dynamic range of each pixel corresponds to 10 bit. In this case, since magnitude of noise becomes relatively smaller as dynamic range of each pixel becomes larger, the value of the threshold value T becomes smaller and the noise removal performance consequently deteriorates as shown by the comparison between FIG. 11B and FIG. 11C. In such a case, the SNR-related data acquisition function 40 may acquire information on the dynamic range of the pixel value and multiply the control signal G by the ratio between the dynamic range at the time of imaging and the dynamic range at the time of training.

Moreover, the image processing system 100 may be configured such that the noise removal or noise reduction performance can be changed by user's adjustment. For instance, a user sets the denoising strength (i.e., parameter value that changes degree of noise removal or noise reduction) via the input device 23 of the image processing system 100. The SNR-related data acquisition function 40 or the parameter adjustment function 50 can change the noise removal or noise reduction performance of the neural network 60 by acquiring the denoising strength having been set by the user and multiplying the control signal G by the denoising strength.

Although FIG. 4 illustrates the case where the control signal is inputted from the parameter adjustment function 50 to every node 80 in each of the intermediate layers 62, the image processing system 100 is not necessarily limited to this configuration. The image processing system 100 may be configured such that the control signal is inputted only to some of the nodes 80. Alternatively, the image processing system 100 may be configured such that only the parameters of some of the nodes 80 are adjusted on the basis of the SNR-related data, while the parameters of the other nodes 80 are fixed to parameter values determined in the learning mode.

Although the Soft-shrinkage function $F_{SS}$ (x, T) shown in FIG. 6A and expressed by the equation (5), or the Hard- Shrinkage function $F_{HS}$ (x, T) shown in FIG. 6B are exemplified as the activation functions used in the present embodiment, various activation functions other than these two functions can also be used for the neural network 60 of the present embodiment.

For instance, a function using the tank function expressed by the following equation (6) may be used as the activation function.

$$f(x, T) = x - T \tanh\left(\frac{x}{T}\right) \qquad \text{Equation (6)}$$

Alternatively, a function using the clipping function $f_{clip}$ expressed by the following equation (7) may be used as the activation function.

$$f(x,T)=x-f_{clip}(x,T,-T) \qquad \text{Equation (7)}$$

Further alternatively, a function using the ReLU function $f$ ReLu expressed by the following equation (8) may be used as the activation function.

$$f(x,T)=f_{ReLU}(f_{ReLU}(X)-T)-f_{ReLU}(f_{ReLU}(-x)-T) \qquad \text{Equation(8)}$$

Other Embodiments

Hereinafter, a description will be given of embodiments of the neural network 60 that has a configuration different from the configuration of the above-described first embodiment.

Figure 13:
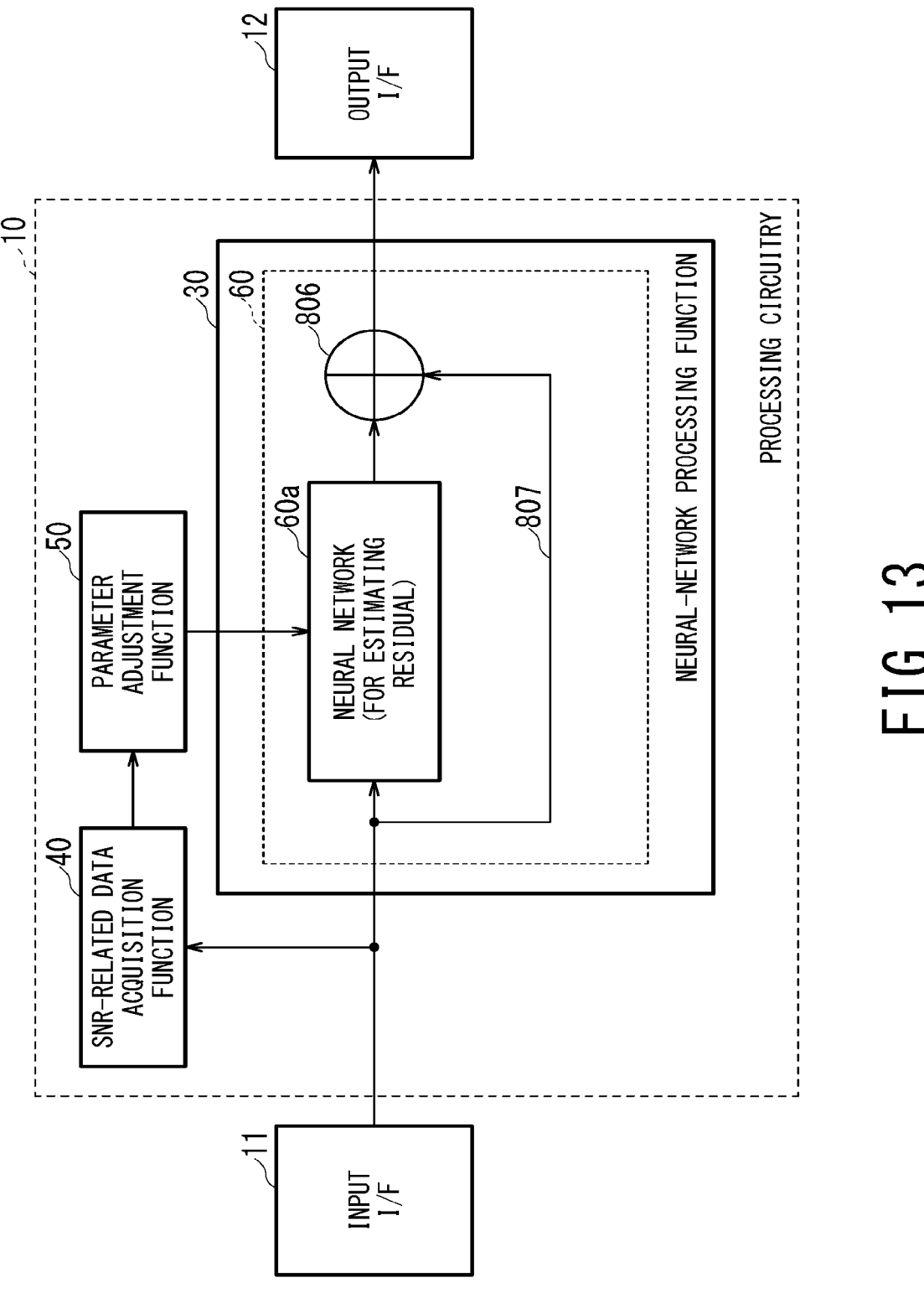
FIG. 13 is a block diagram illustrating a configuration of the image processing system according to the second embodiment.

FIG. 13 is a block diagram illustrating a configuration of the image processing system 100 according to the second embodiment. The block diagram of FIG. 13 shows the configuration focusing on the operation in the image processing mode and in particular, the internal configuration of the neural network 60 related to the image processing mode. Although the input device 23, the memory 21, the display 22, and the parameter learning function 20 among all the components of the image processing system 100 shown in FIG. 1 are omitted in FIG. 13, these components may be included in the image processing system 100 according to the second embodiment.

The neural network 60 of the second embodiment includes a neural network 60a for residual estimation, a path 807 bypassing the neural network 60a, and a subtractor 806 for subtracting the output (residual) of the neural network 60a from the output of the path 807.

The neural network 60a is a neural network generated by residual learning. In this case, the neural network 60a estimates only the residual obtained by removing the signal value from each pixel value of the input image. That is to say, the neural network 60a estimates only the noise component included in the input image. Then, the neural network 60a outputs only the estimated noise component to one end of the subtractor 806.

Meanwhile, the input image including noise is inputted to the other end of the subtractor 806 through the path 807. In the subtractor 806, the noise estimated by the neural network 60a is subtracted from the input image. As a result, the subtractor 806, i.e., the neural network 60 outputs such an image that noise is removed from the input image or noise is reduced.

The neural network 60 of the second embodiment is also configured such that the internal parameters of the neural network 60a can be adjusted for residual estimation on the basis of the input image or the SNR-related data acquired from the supplementary information of the input image.

Thus, even when magnitude of noise in the image used in the learning mode is different from that used in the image processing mode, deterioration of noise removal or noise reduction performance can be prevented.

Figure 14:
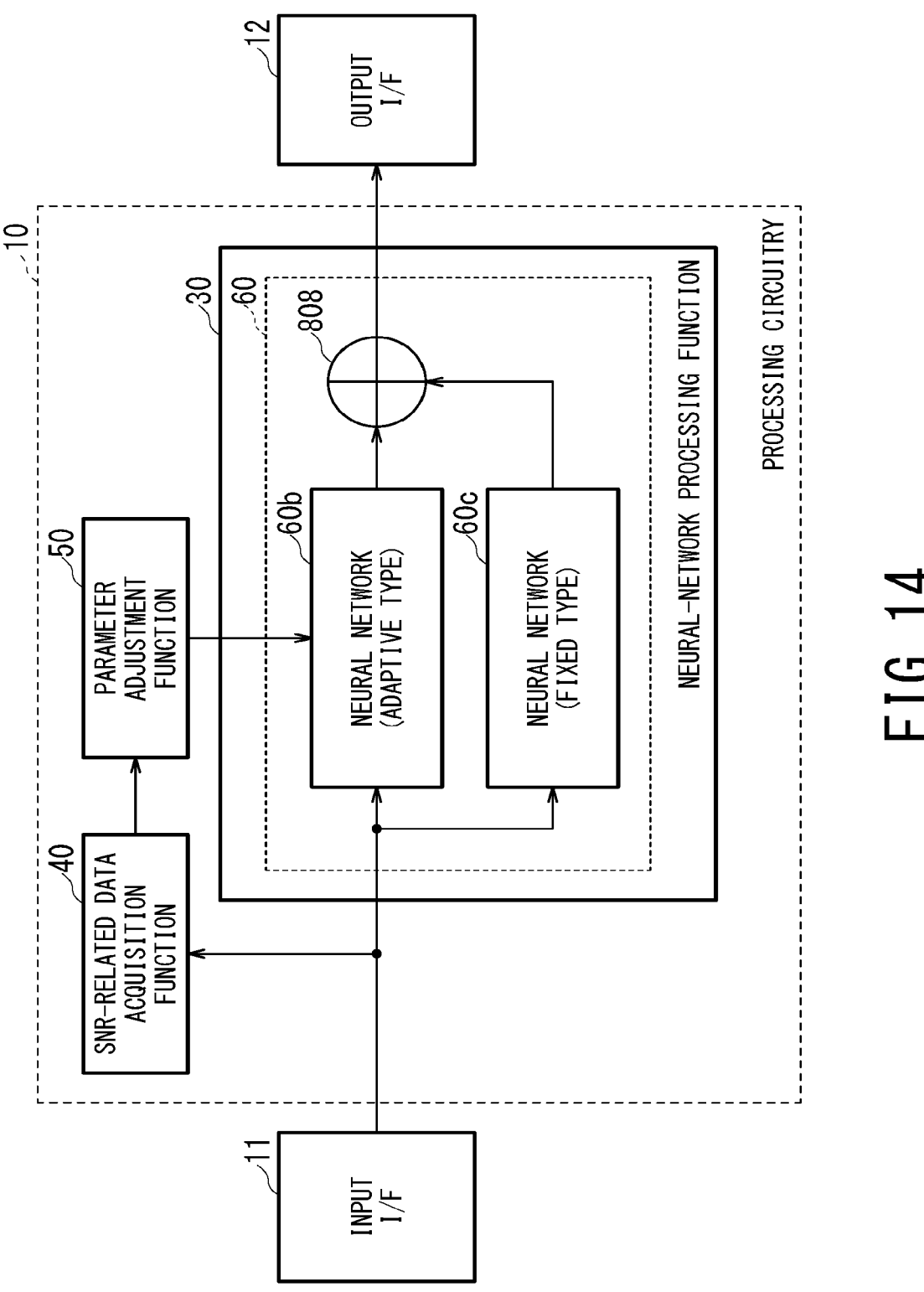
FIG. 14 is a block diagram illustrating a configuration of the image processing system according to the third embodiment.

FIG. 14 is a block diagram illustrating a configuration of the image processing system 100 according to the third embodiment. The block diagram of FIG. 14 also illustrates the configuration focusing on the operation in the image processing mode and in particular, the internal configuration of the neural network 60 related to the image processing mode, similarly to FIG. 13.

The neural network 60 of the third embodiment is configured such that the input to the neural network 60 is divided into two paths to be processed. One path is provided with at least one adaptive-type neural network 60b, and another path is provided with at least one fixed-type neural network 60c. The neural network 60 is further provided with an adder 808 for adding the respective outputs of the two neural networks 60b and 60c.

In the image processing system 100 according to the third embodiment, only the adaptive-type neural network 60b is configured to be able to adjust its internal parameters in the image processing mode on the basis of the SNR-related data acquired from the input image or the supplementary information of the input image. In the meantime, the internal parameters of the fixed-type neural network 60c are fixed to the values determined in the learning mode, even in the image processing mode.

Since noise is removed or reduced in the respective images outputted from the neural network 60b and the neural network 60c, the output I/F 12 outputs such an image that noise is reduced or removed from the inputted image, by adding the image outputted from the neural network 60b to the image outputted from the neural network 60c.

Note that even in the third embodiment, the internal parameters of the neural network 60b are adjusted on the basis of the SNR-related data. Thus, even when noise of the image used in the learning mode is different from that used in the image processing mode, deterioration of noise removal or noise reduction performance can be prevented.

Figure 15:
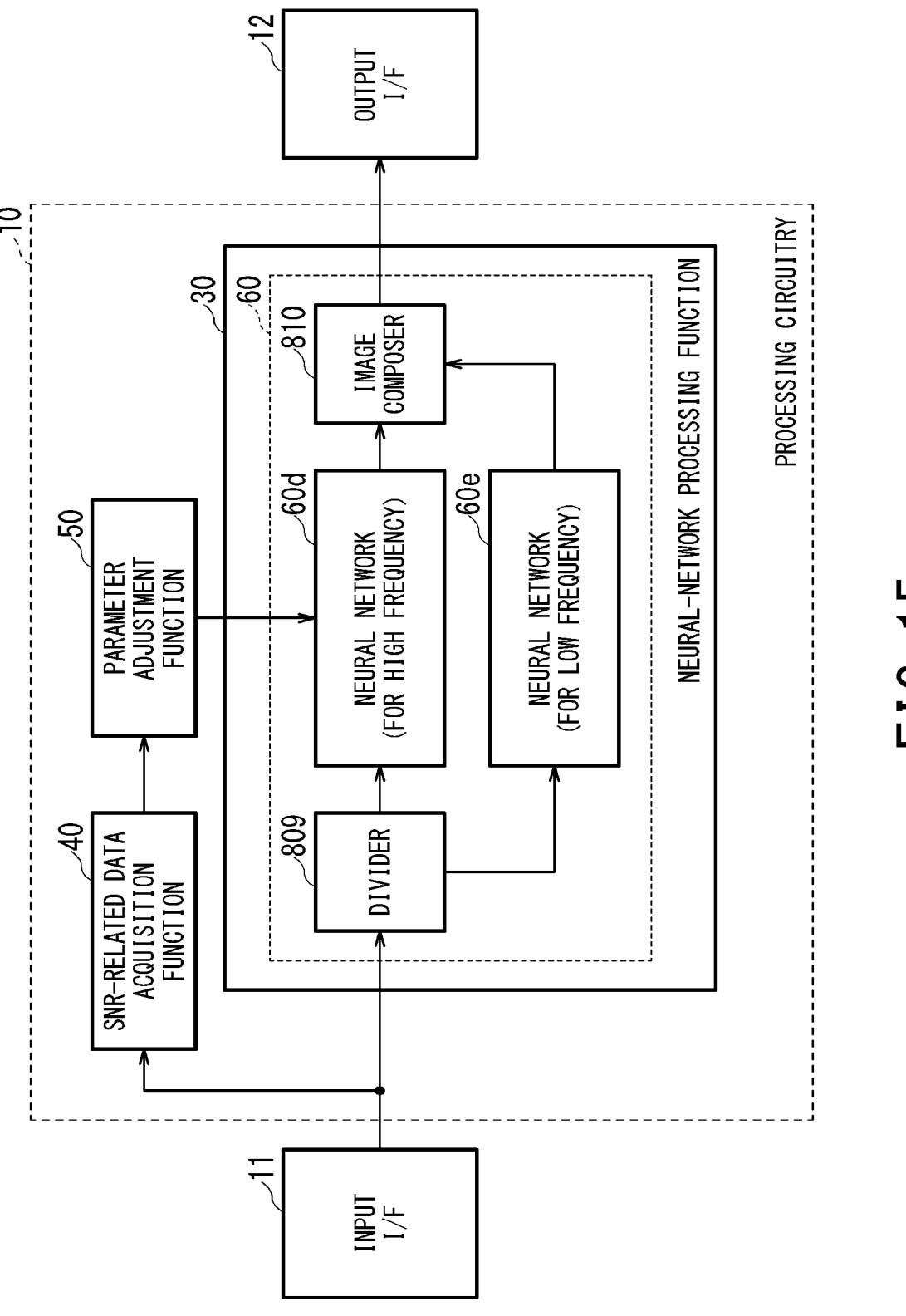
FIG. 15 is a block diagram illustrating a configuration of the image processing system according to the fourth embodiment.

FIG. 15 is a block diagram illustrating a configuration of the image processing system 100 according to the fourth embodiment. The block diagram of FIG. 15 also illustrates the configuration focusing on the operation in the image processing mode, and in particular, the internal configuration of the neural network 60 related to the image processing mode, similarly to FIG. 13. Although the input device 23, the memory 21, the display 22, and the parameter learning function 20 shown in FIG. 1 are omitted in FIG. 15, these components may be included in the image processing system 100 according to the fourth embodiment.

The neural network 60 of the fourth embodiment is configured to divide a frequency region of an input image into a high frequency region and a low frequency region to perform processing on signals of two (or plural) frequency bands. For instance, the neural network 60 of the fourth embodiment 60 includes a divider 809, at least one neural network 60d for high frequency, at least one neural network 60e for low frequency, and an image composer 810.

The divider 809 converts the input image expressed in the real space region into data in the spatial frequency region by performing, e.g., two-dimensional Fourier transform on the input image. Further, the divider 809 divides the transformed data in the spatial frequency region into, e.g., high frequency band data and low frequency band data by applying, e.g., a high pass filter and/or a low pass filter.

Thereafter, the high frequency band data are inputted to the neural network 60d for high frequency and subjected to image processing. The neural network 60d for high frequency may be configured as an internal-parameter adaptive type. That is, the image processing system 100 is configured such that the internal parameters can be adjusted on the basis of the SNR-related data acquired from the input image or the supplementary information of the input image even after training.

On the other hand, the low frequency band data are inputted to the neural network 60e for low frequency and subjected to image processing. The neural network 60e for low frequency may be configured as an internal-parameter fixed type. That is, the internal parameters determined in the learning mode are fixed in the image processing mode, and the input data are processed in this state.

Since noise is removed or reduced in the respective images outputted from the neural networks 60d and 60e, the image composer 810 composes the respective images outputted from the neural networks 60d and 60e so as to cause the output I/F 12 to output such an image that noise is reduced or removed from the inputted image.

Also in the fourth embodiment, the internal parameters of the neural network 60d are adjusted on the basis of the SNR-related data. Thus, even when magnitude of noise used in the learning mode is different from that used in the image processing mode, deterioration of the noise removal or noise reduction performance can be prevented.

Figure 16:
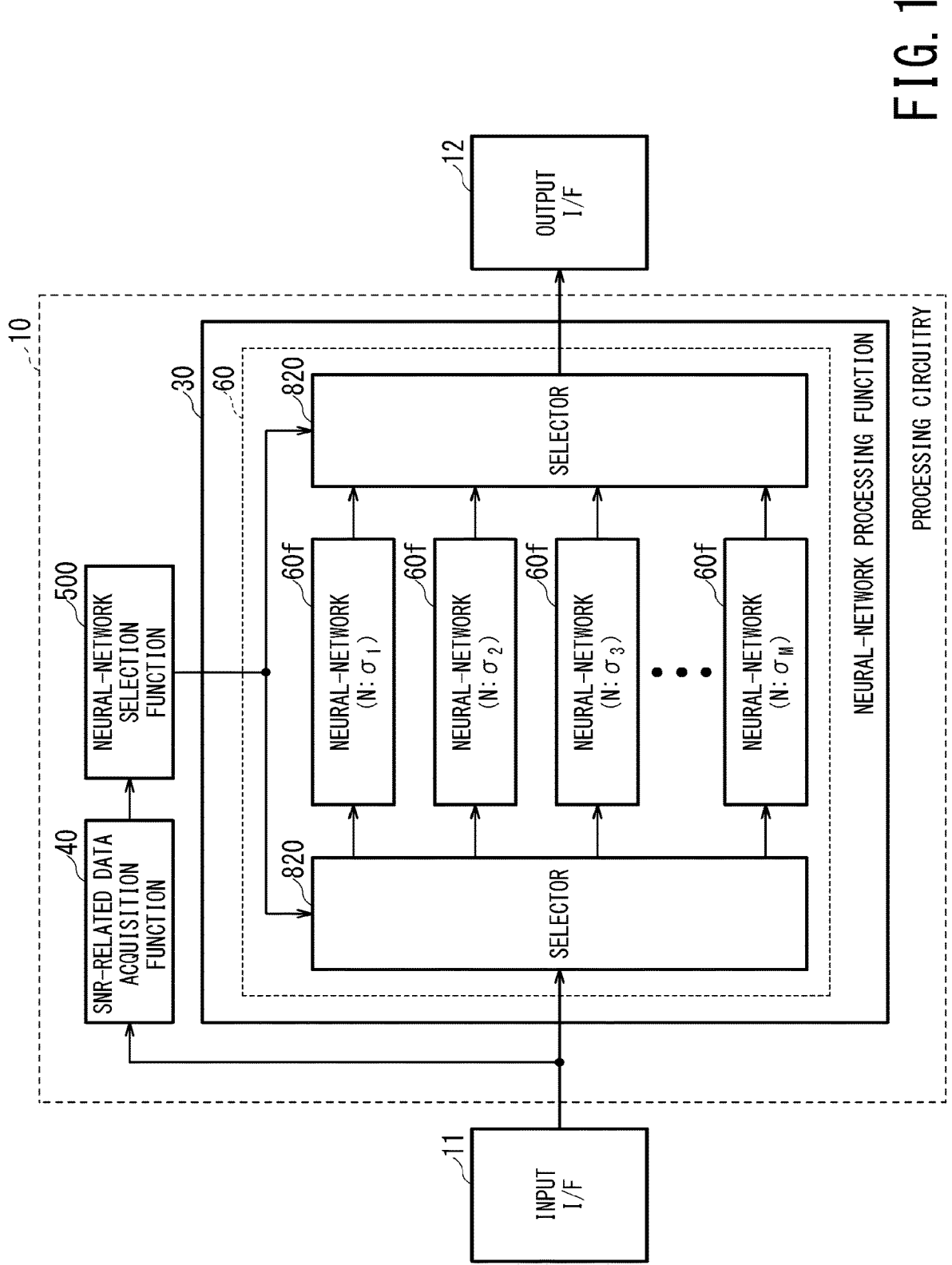
FIG. 16 is a block diagram illustrating a configuration of the image processing system according to the fifth embodiment.

FIG. 16 is a block diagram showing a configuration example of the image processing system 100 according to the fifth embodiment. In the embodiments so far, examples in which the internal parameters of the neural network can be adjusted have been described, but the embodiments are not limited to these examples. For example, in the "learning mode", the image processing system 100 generates neural networks according to the amount of noise using training images classified according to the amount of noise. That is, as shown in FIG. 16, in the "learning mode", the image processing system 100 generates a plurality of neural networks 60f whose internal parameters have been adjusted according to the amount of noise $\sigma_m$ (m=1 to M).

In the meantime, in the "image processing mode", the image processing system 100 determines the amount of noise $\sigma_m$ of the input image based on the SNR-related data acquired from the input image itself or from the additional information of the input image by the SNR-related data acquisition function. Further, the image processing system 100 selects, by the neural network selection function 500 and the selector 820, a neural network 60f whose internal parameters have been adjusted by $\sigma_m$ closest to the determined amount of noise $\sigma$. Using the selected neural network 60f, the image processing system 100 outputs an image in which noise is removed or reduced as compared with the input image.

Figure 17:
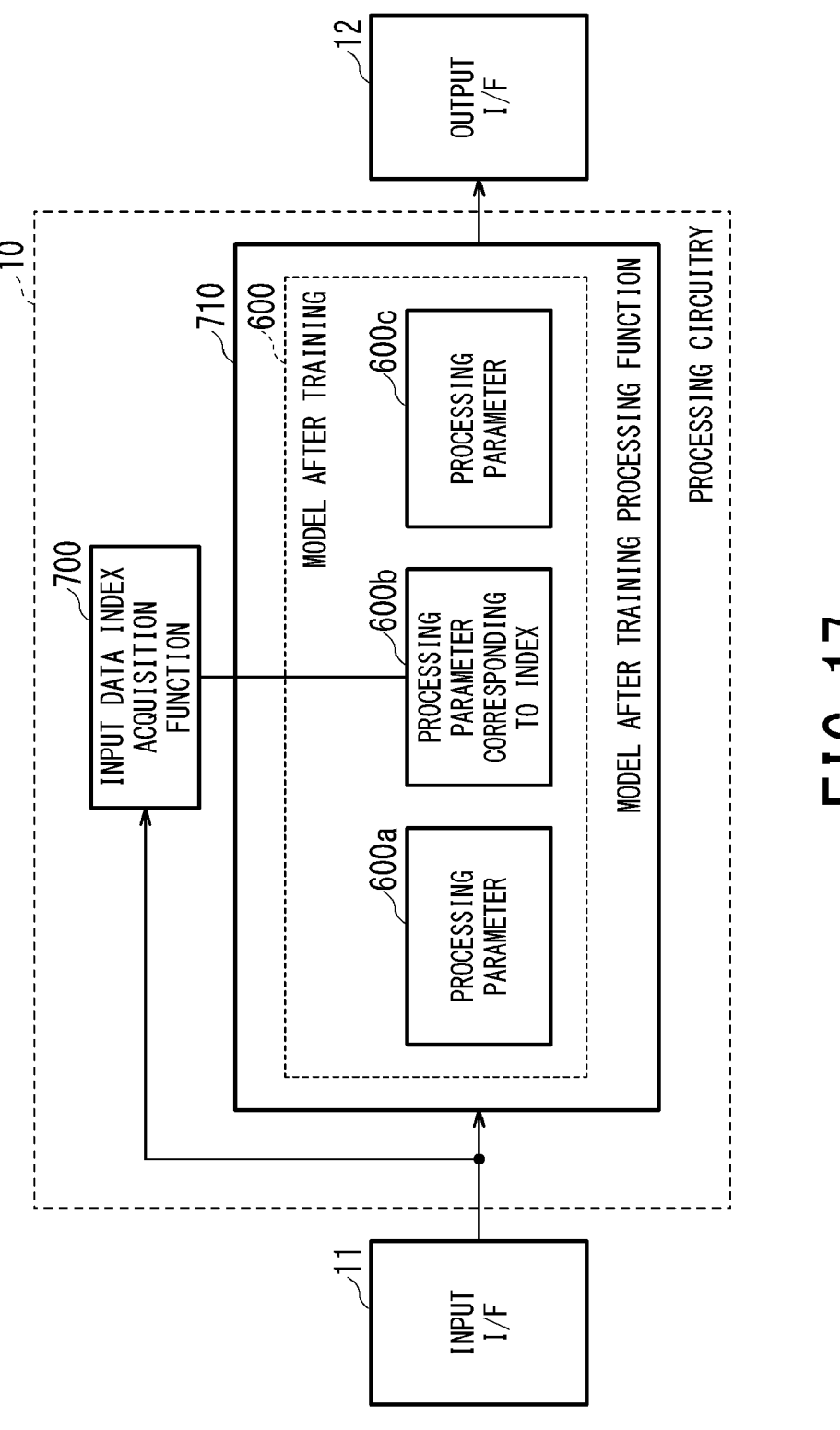
FIG. 17 is a block diagram illustrating a configuration of a medical information processing system to which the image processing system is adapted.

FIG. 17 is a block diagram showing a configuration example of an embodiment in which the image processing system 100 is adapted to a medical information processing system. In the embodiments so far, the neural network has been described as an example of a machine learning model after training, but the embodiment is not limited to this. The model after training obtained by the machine learning is not limited to processing apparatuses in which one or more nodes imitating cells are connected by one or more edges imitating nerves, but may be a function having processing parameters. For example, a model after training obtained by the machine learning may be a regression model such as a linear regression model or a support vector machine (SVM) model, or a tree model such as a decision tree model, a regression tree model, or a random forest model. Incidentally, the model after training includes a model updated by self-training.

In the embodiments so far, the term "input image" is used as a target to be input to the neural network, but this "input image" includes projection data acquired by the CT apparatus, or input data before reconstruction such as k-space data obtained by the MRI apparatus. In FIG. 17, a model after training 600 having processing parameters 600a, 600b, and 600c is illustrated. The input I/F 11 acquires input data obtained by the medical image diagnostic apparatus. Further, the input data index acquisition function 700 acquires an index value related to noise of input data or an index value indicating the property of the input data. The processing parameter 600b is a processing parameter corresponding to the acquired index value. The model after training processing function 710 controls the model after training 600 having the processing parameter 600b corresponding to the index value in the input data so as to process the input data.

In the above-described embodiments, the processing circuitry or the computer constituting the image processing system 100 has been described as being one. However, the number of processing circuitries or computers constituting the image processing system 100 is not limited to one, and the above-described processing may be performed by using plural processing circuitries or plural computers.

According to at least one embodiment described above, even when the amount of noise superimposed on an image at the time of use is different from the amount of noise of the training image in the image processing system that uses the neural network, high noise removal or high noise reduction performance can be secured.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical information processing system comprising:
a memory configured to store a predetermined program; and
processing circuitry configured, by executing the predetermined program, to
(a) in a training phase, create a neural network by a machine learning,
wherein the neural network comprises an input layer, an output layer, and an intermediate layer provided between the input layer and the output layer, wherein the intermediate layer includes at least one node having at least one first internal parameter T, and the first internal parameter T is determined by a second internal parameter a and by a control signal G, and the first internal parameter T and the second internal parameter a are determined through the machine learning in the training phase with the control signal G being fixed value;
(b) in an inference phase conducted after the training phase,

accept denoising strength that changes degree of noise removal or noise reduction, the denoising strength being set by a user,
input an input data obtained by a medical imaging apparatus into the neural network,
adjust the first internal parameter T based on the control signal G calculated from SNR-related data related to the input data, the denoising strength, and the second internal parameter a, the second internal parameter a having been determined in the training phase,
denoise the input data using the neural network with the adjusted first internal parameter T, and
output an output data denoised from the input data.

2. The medical information processing system according to claim 1,
wherein the input data is an image that includes noise; and
the processing circuitry is configured to perform processing on the input data in such a manner that the noise is reduced or removed from the input data.

3. The medical information processing system according to claim 1,
wherein the node has an activation function; and
the first internal parameter T is a parameter of the activation function.

4. The medical information processing system according to claim 3,
wherein the activation function is a function of removing such an input signal included in the input data that amplitude thereof is smaller than a threshold value; and
the first internal parameter T is the threshold value of the activation function.

5. The medical information processing system according to claim 3,
wherein the activation function is a function that outputs zero in a case of receiving an input value within a range including zero and outputs a value proportional to an input value in a case of receiving an input value outside the range.

6. The medical information processing system according to claim 1,
wherein the neural network includes a first neural network and a second neural network; and
the processing circuitry is configured to adjust the first internal parameter T of the first neural network based on the control signal G calculated from the SNR-related data related to the input data, and does not adjust the first internal parameter T of the second neural network.

7. The medical information processing system according to claim 1,
wherein, the medical information processing system is configured as at least one computer.

8. The medical information processing system according to claim 1,
wherein, the medical information processing system is configured as at least one of an MRI apparatus, a CT apparatus, and an ultrasound diagnostic apparatus.

9. The medical information processing system according to claim 1, wherein in the inference phase,
the processing circuitry is further configured to adjust the first internal parameter T based on product of the second internal parameter a and the control signal G, and the control signal G is further multiplied by the denoising strength set by the user.

10. The medical information processing system according to claim 1, wherein in the training phase,
the processing circuitry is further configured to determine the first internal parameter T based on product of the second parameter a and the control signal G, wherein
the fixed value of the control signal G is 1.

* * * * *